United States Patent
Nguyen-Kim et al.

(10) Patent No.: US 7,829,070 B2
(45) Date of Patent: Nov. 9, 2010

(54) AMPHOLYTIC ANIONIC COPOLYMERS

(75) Inventors: Son Nguyen-Kim, Hemsbach (DE);
Klemens Mathauer, Heidelberg (DE);
Claudia Wood, Weinheim (DE); Gerd Schuh, Schwegenheim (DE); Darshan Patwardhan, Neuhofen (DE)

(73) Assignee: BASF SE, Ludwigshafen (DE)

(*) Notice: Subject to any disclaimer, the term of this patent is extended or adjusted under 35 U.S.C. 154(b) by 1127 days.

(21) Appl. No.: 10/582,227

(22) PCT Filed: Dec. 8, 2004

(86) PCT No.: PCT/EP2004/013983

§ 371 (c)(1),
(2), (4) Date: Jun. 9, 2006

(87) PCT Pub. No.: WO2005/058988

PCT Pub. Date: Jun. 30, 2005

(65) Prior Publication Data

US 2007/0141013 A1    Jun. 21, 2007

(30) Foreign Application Priority Data

Dec. 9, 2003 (DE) ................ 103 57 487

(51) Int. Cl.
*A61K 8/81* (2006.01)
*C08F 20/06* (2006.01)
(52) U.S. Cl. .............. 424/70.16; 526/317.1; 526/318.4; 526/328; 526/328.5
(58) Field of Classification Search .............. 424/70.16; 526/317.1, 318.4, 328, 328.5
See application file for complete search history.

(56) References Cited

U.S. PATENT DOCUMENTS

| | | | |
|---|---|---|---|
| 3,927,199 A | 12/1975 | Micchelli et al. | |
| 4,237,253 A | 12/1980 | Jacquet et al. | |
| 4,767,613 A | 8/1988 | Nuber et al. | |
| 5,840,804 A | 11/1998 | Carl et al. | |
| 6,407,158 B1 | 6/2002 | Kim et al. | |
| 6,482,393 B1 | 11/2002 | Schehlmann et al. | |
| 7,015,294 B2 * | 3/2006 | Dausch et al. | 526/319 |
| 2005/0265950 A1 | 12/2005 | Chrisstoffels et al. | |
| 2007/0116660 A1 | 5/2007 | Kim et al. | |

FOREIGN PATENT DOCUMENTS

| | | |
|---|---|---|
| EP | 0 183 466 | 6/1986 |
| WO | WO-9535087 | 12/1995 |
| WO | WO-0039176 | 7/2000 |
| WO | WO-0162809 | 8/2001 |
| WO | WO-0241856 | 5/2002 |
| WO | WO-02083085 | 10/2002 |
| WO | WO-2004058837 | 7/2004 |
| WO | WO-2005005497 | 1/2005 |

* cited by examiner

*Primary Examiner*—David Wu
*Assistant Examiner*—Vu A Nguyen
(74) *Attorney, Agent, or Firm*—Connolly Bove Lodge & Hutz LLP

(57) ABSTRACT

Ampholytic copolymers which contain a molar excess of anionogenic and/or anionic groups, polyelectrolyte complexes which contain such an ampholytic copolymer, cosmetic and pharmaceutical compositions which contain at least one such copolymer or polyelectrolyte complex and the use of these copolymers and polyelectrolyte complexes are described.

53 Claims, No Drawings

AMPHOLYTIC ANIONIC COPOLYMERS

The present invention relates to ampholytic copolymers which comprise a molar excess of anionogenic and/or anionic groups, polyelectrolyte complexes which comprise such an ampholytic copolymer, cosmetic and pharmaceutical compositions which comprise at least one such copolymer or polyelectrolyte complex and the use of these copolymers and polyelectrolyte complexes.

Polymers having a relatively large number of ionically dissociable groups in the main chain and/or a side chain are referred to as polyelectrolytes. If these polymers have both anionogenic/anionic and cationogenic/cationic groups, they are amphoteric polyelectrolytes or ampholytic polymers. These may comprise oppositely charged/chargeable groups in equimolar amounts or a molar excess of one of the species. Thus, the expression "anionic ampholytic copolymers" represents ampholytic copolymers which comprise a molar excess of anionogenic and/or anionic groups. An ionogenic or ionic polymer can react with an oppositely chargeable or charged polymer with formation of a polyelectrolyte complex (symplex). Ampholytic polymers can in principle form such polyelectrolyte complexes with at least one further anionogenic/anionic, cationogenic/cationic and/or ampholytic polymer. Polyelectrolytes having a sufficient number of dissociable groups are water-soluble or water-dispersible and have a variety of applications in surface coatings, paper assistants, in textile production and especially in pharmacy and cosmetics.

Cosmetically and pharmaceutically acceptable water-soluble polymers are used, for example, in soaps, creams and lotions as formulation compositions, for example as thickeners, foam stabilizers or water absorbents or for reducing the irritant effect of other ingredients or for improving the dermal application of active substances. Their task in hair cosmetics is to influence the properties of the hair. In pharmacy, they serve, for example, as coating materials or binders for solid dosage forms.

For hair cosmetics, film-forming polymers are used, for example as conditioners, for improving the dry and wet combability, handle, gloss and appearance and for imparting antistatic properties to the hair. It is known that water-soluble polymers having cationic functionalities can be used in hair conditioners which have a relatively great affinity to the structurally related negatively charged surface of the hair and prevent electrostatic charge build-up on the hair. The structure and mode of action of various hair treatment polymers are described in Cosmetic & Toiletries 103 (1988), 23. Commercial cationic conditioner polymers are, for example, cationic hydroxyethylcellulose, cationic polymers based on N-vinylpyrrolidone, e.g. copolymers of N-vinylpyrrolidone and quaternized N-vinylimidazole or copolymers of acrylamide and diallyldimethylammonium chloride.

For hair cosmetics, film-forming polymers are furthermore used as setting resins for holding the hairstyle. Requirements for setting resins are, for example, strong setting at high atmospheric humidity, elasticity, capability of being washed out from the hair, compatibility in the formulation and a pleasant handle of the hair treated therewith. For setting hairstyles, for example, vinyllactam homo- and copolymers and carboxylate-containing polymers are used.

The provision of products having a complex property profile often presents difficulties. Thus, there is a need for polymers for cosmetic hair compositions which are capable of forming substantially smooth, nontacky films which have a good setting effect on the hair (even at high atmospheric humidity) and at the same time impart good sensory properties, such as elasticity and a pleasant handle, to the hair. If these polymers are to be used in hairspray formulations, good compatibility with the propellant, suitability for use in low-VOC formulations, good solubility in water or aqueous/alcoholic solvent mixtures and good washout properties are also desirable.

In many cases, the desired property profile can be achieved only by using a plurality of cosmetically active components, for example a plurality of polymers having ionic groups. However, incompatibility of the various components with one another is frequently found, which may mean that, for example, it is no longer possible to prepare clear formulations. A plurality of polyelectrolytes not sufficiently compatible with one another can lead to undesired salting out. There is therefore a need for cosmetically and pharmaceutically tolerated polyelectrolytes which, when used as the only polymer component, are suitable for providing a certain property profile and/or are compatible with a large number of different components, in particular polyelectrolytes.

It is known that polymers based on tert-butyl (meth)acrylate can be used in hair cosmetics. Thus, EP-A-0 257 444 describes terpolymers of tert-butyl (meth)acrylate, vinylpyrrolidone and (meth)acrylic acid and cosmetic hair compositions comprising them. WO 94/24986 describes a hair setting composition which comprises, as a film former, a copolymer which comprises tert-butyl (meth)acrylate, (meth)acrylic acid and, if appropriate, further monomers incorporated in the form of polymerized units, at least one of the additional monomers giving a homopolymer having a glass transition temperature of less than 30° C.

EP-A-183 466 describes a process for the preparation of a polymer dispersion by polymerization of a water-soluble monomer in an aqueous salt-containing medium in the presence of a dispersant. The water-soluble monomer may be, inter alia, an ethylenically unsaturated compound having a cationic or anionic group. Dispersants which may be used are polyelectrolytes whose ionogenic/ionic groups must correspond to the charge of the monomers used.

EP-A-670 333 describes crosslinked water-soluble polymer dispersions which are obtainable by polymerization of a monomer mixture comprising at least one water-soluble monomer, at least one crosslinking agent and, if appropriate, hydrophobic and/or amphiphilic monomers in the presence of a polymeric dispersant. Water-soluble monomers which may be used are, in addition to a large number of further monomers, also N-vinylpyrrolidone and monomers having cationic/cationizable groups, such as N-vinylimidazole. The polymeric dispersants may be polyelectrolytes which comprise, for example, salts of (meth)acrylic acid as anionic monomer building blocks or quaternized derivatives of N,N-dimethylaminoethyl (meth)acrylate as cationic building blocks incorporated in the form of polymerized units. A use of the polymer dispersions in cosmetics is not described.

WO 00/39176 describes a hydrophilic cationic ampholytic copolymer which comprises from 0.05 to 20 mol % of an anionic monomer having at least one carboxyl group and from 10 to 45 mol % of a cationic monomer having at least one amino group incorporated in the form of polymerized units, the molar ratio of cationic to anionic monomer being from about 2:1 to 16:1. These ampholytic copolymers can be used, inter alia, for modifying the rheological properties of personal hygiene compositions.

WO 02/41856 describes the use of polymer dispersions which are obtainable by polymerization of at least one water-soluble monomer in an aqueous salt solution which comprises at least one polyelectrolyte as a dispersant for the cosmetic treatment of keratinic materials. In addition, the dispersions comprise at least one agent for adjusting the viscosity, for example a polycarboxylic acid or a salt thereof. Water-soluble monomers which may be used are cationic, anionic and nonionic monomers, monomer mixtures which comprise at least one cationic monomer and, if appropriate, additionally acrylic acid and/or acrylamide being preferred.

WO 02/083085 describes a cosmetic composition comprising a dispersion of a cationic, anionic or nonionic polymer in an aqueous salt solution.

EP-A-1038891 describes water-soluble or water-dispersible polymeric salts of at least one polymer and at least one oppositely charged neutralizing agent.

WO 01/62809 describes a cosmetic composition which comprises at least one water-soluble or water-dispersible polymer which incorporates
  a) from 5 to 50% by weight of at least one α,β-ethylenically unsaturated monomer having a tert-butyl group,
  b) from 25 to 90% by weight of at least one N-vinylamide and/or N-vinyllactam,
  c) from 0.5 to 30% by weight of at least one compound having an α,β-ethylenically unsaturated double bond capable of free radical polymerization and at least one cationogenic and/or cationic group per molecule, and
  d) from 0 to 30% by weight of at least one further α,β-ethylenically unsaturated compound, it being possible for said compound to be a compound having at least one anionogenic and/or anionic group per molecule.

U.S. Pat. No. 3,927,199 describes a hair setting composition which comprises a film-forming binder resin based on a copolymer which comprises 1) N-alkylacrylamides or -methacrylamides, 2) monomers containing acid groups and 3) at least one further comonomer incorporated in the form of polymerized units.

U.S. Pat. No. 4,237,253 describes copolymers for hair treatment compositions which comprise from 22 to 64 mol % of N,N-dimethylamino-2-ethyl methacrylate, from 13 to 71 mol % of methyl methacrylate, from 6 to 23 mol % of methacrylic acid and up to 22 mol % of further monomers incorporated in the form of polymerized units.

WO 95/35087 describes an amphoteric hair setting polymer for use in hairsprays and gels, which comprises from 40 to 90% by weight of a hydroxyl-containing monomer, from 1 to 20% by weight of a monomer containing acid groups and from 1 to 20% by weight of an amino-containing monomer incorporated in the form of polymerized units.

The unpublished German Patent Application P 102 61 750.3 describes an ampholytic copolymer which is obtainable by free radical copolymerization of
  a) at least one ethylenically unsaturated compound having at least one anionogenic and/or anionic group,
  b) at least one ethylenically unsaturated compound having at least one cationogenic and/or cationic group,
  c) at least one unsaturated amido-containing compound
and, if appropriate, further comonomers. Polyelectrolyte complexes which comprise such an ampholytic copolymer and cosmetic or pharmaceutical compositions based on these ampholytic copolymers and polyelectrolyte complexes are furthermore described.

The unpublished German Patent Application 102 37 378.7 describes the use of polymers which are obtainable by
  (i) free radical copolymerization of monomer mixtures comprising.
    (a) at least one cationic monomer or quaternizable monomer,
    (b) if appropriate a water-soluble monomer,
    (c) if appropriate a further monomer capable of free radical copolymerization,
    (d) at least one monomer acting as a crosslinking agent and having at least two ethylenically unsaturated, nonconjugated double bonds, and
    (e) at least one regulator,
  (ii) subsequent quaternization or protonation of the polymer, if a nonquaternizable or only partially quaternizable monomer is used as monomer (a),
in cosmetic hair formulations.

The unpublished German Patent Application 103 31 865.8 describes an aqueous polymer dispersion Pd) which is obtainable by free radical polymerization of a monomer mixture M) comprising
  a) at least one α,β-ethylenically unsaturated amido-containing compound of the formula I

where
    $R^2$ is a group of the formula $CH_2=CR^4—$ and $R^1$ and $R^3$, independently of one another, are H, alkyl, cycloalkyl, heterocycloalkyl, aryl or hetaryl, or $R^1$ and $R^3$ together with the amido group to which they are bonded form a lactam having 5 to 8 ring atoms,
  b) at least one crosslinking compound capable of free radical polymerization and having at least two α,β-ethylenically unsaturated double bonds per molecule,
  c) at least one compound having an α,β-ethylenically unsaturated double bond capable of free radical polymerization and at least one cationogenic and/or cationic group per molecule,
in an aqueous medium in the presence of at least one polymeric anionic dispersant D). They are suitable as conditioners for cosmetic formulations, in particular shampoos.

The unpublished German Patent Application 102 37 378.7 describes a cosmetic or pharmaceutical composition which comprises at least one polyelectrolyte complex which comprises, as component A1), at least one water-soluble or water-dispersible copolymer having cationogenic groups, which comprises vinylimidazole and/or a derivative thereof and at least one further monomer copolymerizable therewith incorporated in the form of polymerized units, and, as component A2), at least one polymer containing acid groups.

In spite of the extensive efforts, there is still a need for improvement in the case of the polymers known from the prior art for the production of elastic hairstyles with simultaneously strong setting (also at high atmospheric humidity). For a promising use in hairspray formulations, good propellant compatibility, good solubility in water or aqueous/alcoholic solvent mixtures, suitability for use in low-VOC formulations and good washout properties are also desirable. Good properties are also desirable with respect to the conditioning of the hair in its sensory properties, such as handle, volume, handleability, etc. Furthermore, the polymers should have good compatibility with other formulation components.

It has surprisingly been found that ampholytic copolymers which comprise a molar excess of anionogenic and/or anionic groups and which are obtainable by free radical polymerization of a) at least one branched $C_3$- to $C_5$-alkyl acrylate,
b) acrylic acid and/or methacrylic acid
c) a monomer composition comprising
  c1) at least one compound having an $\alpha,\beta$-ethylenically unsaturated double bond capable of free radical polymerization and at least one anionogenic and/or anionic group per molecule and
  c2) at least one compound having an $\alpha,\beta$-ethylenically unsaturated double bond capable of free radical polymerization and at least one cationogenic and/or cationic group per molecule,
the molar ratio of anionogenic and anionic groups of the components c1) to cationogenic and cationic groups of the component c2) being about 1:1.

Below, compounds which are derived from acrylic acid and methacrylic acid can in some cases be abbreviated by introducing the syllable "(meth)" into the compound derived from acrylic acid.

In the context of the present invention, water-soluble monomers and polymers are understood as meaning monomers and polymers which have a solubility of at least 1 g/l at 20° C. in water. Water-dispersible monomers and polymers are understood as meaning monomers and polymers which disintegrate into dispersible particles with the application of shear forces, for example by stirring. Hydrophilic monomers are preferably water-soluble or at least water-dispersible. The novel copolymers are generally water-soluble.

For establishing certain product properties of the copolymers, the monomers a) can be partly replaced by at least one monomer e), as defined below. In a special embodiment, up to 50% by weight of the monomers of component a) can then be replaced by at least one $C_1$-$C_3$-alkyl methacrylate and/or hydroxy-$C_1$-$C_3$-alkyl methacrylate. Suitable $C_1$-$C_3$-alkyl methacrylates and hydroxy-$C_1$-$C_3$-alkyl methacrylates are described below for component e). Ethyl methacrylate is preferably used.

The monomer mixture used for the preparation of the novel copolymers comprises monomers having cationogenic and/or cationic groups and monomers having anionogenic and/or anionic groups. The amount of monomers having anionogenic and/or anionic groups which are used for the polymerization is such that, based on the monomers used altogether for the polymerization, the mole fraction of anionogenic and anionic groups is greater than the mole fraction of cationogenic and cationic groups. The novel copolymers therefore have on average a molar excess of anionogenic/anionic groups compared with cationogenic/cationic groups. Preferably, the molar ratio of anionogenic/anionic groups to cationogenic/cationic groups is at least 1.5:1, in particular at least 2:1.

Surprisingly, it has been found that copolymers having particularly advantageous properties are obtained if the cationogenic/cationic monomers c2) are used together with anionogenic/anionic monomers c1) in the form of a monomer composition, i.e. in the form of salt pairs, for the polymerization. The molar ratio of anionogenic and anionic groups of the component c1) to cationogenic and cationic groups of the component c2) is preferably from 0.95:1 to 1.05:1. The salt pairs are externally substantially electroneutral. Acrylic acid and/or methacrylic acid can also be used as monomer c1) in the monomer composition c). Even then, further acrylic acid and/or methacrylic acid (=component b) is additionally used for the polymerization.

For the preparation of the novel copolymers, the acrylic acid or methacrylic acid b) can be used in partly or completely deprotonated form. The opposite ions thereof are then preferably derived from bases, as described below for adjusting the pH during the polymerization or of the polymers obtained.

The novel copolymers are particularly advantageous for use in cosmetic compositions, in particular in hair treatment compositions. They are preferably used for producing elastic hairstyles in combination with strong setting. Advantageously, they are also distinguished both by good propellant compatibility and by good solubility in water or aqueous/alcoholic solvent mixtures. They can therefore be formulated both to give hairsprays having a low water content (VOC at least 85% by weight) and formulations having a high water content, i.e. low VOC values (in general not more than 55% by weight, based on the total weight of the composition). In every case, the hairspray formulation has very good sprayability.

Monomer a)

The novel copolymers comprise at least one compound which is incorporated in the form of polymerized units and is preferably selected from isopropyl acrylate, sec-butyl acrylate, isobutyl acrylate, tert-butyl acrylate, 2-pentyl acrylate, 3-pentyl acrylate, isopentyl acrylate, neopentyl acrylate and mixtures thereof. tert-Butyl acrylate and mixtures which comprise tert-butyl acrylate are particularly preferred.

The novel copolymers preferably comprise from 20 to 90, particularly preferably from 25 to 85% by weight, based on the total weight of the monomers used for the polymerization, of at least one monomer a) incorporated in the form of polymerized units.

It has surprisingly been found that copolymers having particularly advantageous properties are obtained if a part of the monomers a) is replaced by at least one further monomer which is selected from tert-butyl methacrylate, N-tert-octylacrylamide, N-tert-butylacrylamide and mixtures thereof. Preferably, not more than 50, particularly preferably not more than 40, in particular not more than 30% by weight of the monomers a) are replaced by at least one of said further monomers. The amount of these further monomers is preferably not more than 30, particularly preferably not more than 25% by weight, based on the total weight of the monomers used for the preparation of the novel copolymers. Polymers based on these monomer mixtures have very good film formation properties. The films obtained are hard and nontacky and can be readily washed out.

Monomer b)

The novel copolymers preferably comprise from 5 to 40, particularly preferably from 10 to 35, in particular from 13 to 30% by weight, based on the total weight of the monomers used for the polymerization, of acrylic acid and/or methacrylic acid (=monomer b) incorporated in the form of polymerized units.

It has surprisingly been found that copolymers having particularly advantageous properties are obtained if a part of the acrylic acid is replaced by methacrylic acid. Preferably not more than 65, particularly preferably not more than 50% by weight of acrylic acid are replaced by methacrylic acid. The amount of methacrylic acid is preferably not more than 20, particularly preferably not more than 17% by weight, based on the total weight of the monomers used for the preparation of the novel copolymers. Polymers based on acrylic acid/methacrylic acid mixtures likewise have very good film formation properties. The films obtained are hard and nontacky and can be readily washed out.

In a special embodiment, component b) consists only of acrylic acid or only of methacrylic acid.

Monomer Composition c)

The novel copolymers preferably comprise from 0.5 to 25, particularly preferably from 1 to 20, in particular from 2 to 16% by weight, based on the total weight of the monomers used for the polymerization, of a monomer composition c) incorporated in the form of polymerized units. Said amounts by weight are all based on the free acid form or the free base form of the monomers c1) and c2).

Monomer c1)

The monomer composition c) comprises, as component c1), at least one compound having an α,β-ethylenically unsaturated double bond capable of free radical polymerization and at least one anionogenic and/or anionic group per molecule.

Preferably, the compounds c1) are selected from α,β-ethylenically unsaturated mono- and dicarboxylic acids, sulfonic acids, phosphonic acids and mixtures thereof.

The monomers c1) include monoethylenically unsaturated mono- and dicarboxylic acids of 3 to 25, preferably 3 to 6, carbon atoms, which can also be used in the form of their salts or anhydrides. Examples of these are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. The monomers c1) furthermore include the monoesters of monoethylenically unsaturated dicarboxylic acids, e.g. of maleic acid, such as monomethyl maleate. The monomers c1) also include monoethylenically unsaturated sulfonic acids and phosphonic acids, for example vinylphosphonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, 2-acrylamido-2-methylpropanesulfonic acid, vinylphosphonic acid and allylphosphonic acid. The monomers c1) are preferably used in protonated (uncharged) form for providing the monomer composition c). However, the suitable monomers c1) also include the salts of the abovementioned acids, in particular the sodium, potassium and ammonium salts and the salts with the abovementioned amines. The abovementioned amounts by weight are all based on the free acid form. The monomers c1) can be used in the monomer composition c) as such or as mixtures with one another.

The component c1) is preferably selected from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof.

The component c1) is particularly preferably selected from acrylic acid, methacrylic acid, itaconic acid, crotonic acid and mixtures thereof.

Monomer c2)

The monomer composition c) comprises, as component c2), at least one compound having an α,β-ethylenically unsaturated double bond capable of free radical polymerization and at least one cationogenic and/or cationic group per molecule.

The cationogenic or cationic groups of component c2) are preferably nitrogen-containing groups, such as primary, secondary and tertiary amino groups and quaternary ammonium groups. The nitrogen-containing groups are preferably tertiary amino groups. The compounds c2) are preferably used in uncharged form for providing the monomer composition c). However, the use in charged form is also suitable. Charged cationic groups can be produced, for example, from the amine nitrogens by protonation, for example with monobasic or polybasic carboxylic acids, such as lactic acid or tartaric acid, or mineral acids, such as phosphoric acid, sulfuric acid and hydrochloric acid.

The component c2) is preferably selected from esters of α,β-ethylenically unsaturated mono- and dicarboxylic acids with amino alcohols which can be mono- or dialkylated on the amine nitrogen, amides of α,β-ethylenically unsaturated mono- and dicarboxylic acids with diamines, which have at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds and mixtures thereof.

The esters of α,β-ethylenically unsaturated mono- and dicarboxylic acids with amino alcohols are suitable as compounds c2). Preferred amino alcohols are $C_2$-$C_{12}$-amino alcohols which are $C_1$-$C_8$-mono- or dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Acrylic acid, methacrylic acid and mixtures thereof are preferably used. N-Methylaminoethyl (meth)acrylate, N-ethylaminoethyl (meth)acrylate, N-(n-propyl)aminoethyl (meth)acrylate, N-(n-butyl)aminoethyl (meth)acrylate, N-(tert-butyl)aminoethyl (meth)acrylate, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate and N,N-dimethylaminocyclohexyl (meth)acrylate are particularly preferred as compounds c2). In particular, N-(tert-butyl)aminoethyl acrylate and N-(tert-butyl)aminoethyl methacrylate are used as compound c2).

Suitable monomers c2) are furthermore the amides of the abovementioned α,β-ethylenically unsaturated mono- and dicarboxylic acids with diamines, which have at least one primary or secondary amino group. Diamines which have a tertiary and a primary or secondary amino group are preferred. N-[2-(Dimethylamino)ethyl]-acrylamide, N-[2-(dimethylamino)ethyl]methacrylamide, N-[3-(dimethylamino)propyl]acrylamide, N-[3-(dimethylamino)propyl]methacrylamide, N-[4-(dimethyl-amino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide are preferably used as monomers c2). N-[3-(Dimethyl-amino)propyl]acrylamide and/or N-[3-(dimethylamino)propyl]-methacrylamide are particularly preferably used.

Suitable monomers c2) are furthermore N,N-diallylamines and N,N-diallyl-N-alkylamines and the acid addition salts thereof. Alkyl is preferably $C_1$-$C_{24}$-alkyl. For example, N,N-diallyl-N-methylamine is preferred.

Suitable monomers c2) are furthermore vinyl- and allyl-substituted nitrogen heterocycles, such as N-vinylimidazole, N-vinylimidazole derivatives, e.g. N-vinyl-2-methylimidazole, vinyl- and allyl-substituted heteroaromatic compounds, such as 2- and 4-vinylpyridine, 2- and 4-allylpyridine, and the salts thereof.

Preferred monomers c2) are N-vinylimidazoles of the formula (I), where $R^1$ to $R^3$ are hydrogen, $C_1$-$C_4$-alkyl or phenyl

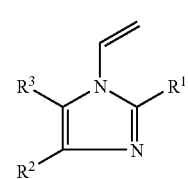

(I)

Examples of compounds of the formula (I) are shown in table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

N-Vinylimidazole and mixtures which comprise N-vinylimidazole are particularly preferred as component c2). These mixtures preferably additionally comprise at least one compound which is selected from N-(tert-butylamino)ethyl (meth)acrylate, N,N-dimethylaminoethyl (meth)acrylate, N-[3-(dimethylamino)propyl](meth)acrylamide and mixtures thereof.

In a special embodiment, the novel copolymers consist only of monomer units of the abovementioned monomers a), b) and c). In further embodiments, the novel copolymers comprise additional monomers incorporated in the form of polymerized units. Suitable additional monomers are described below.

Monomer d)

The copolymer preferably additionally comprises at least one N-vinyllactam d) incorporated in the form of polymerized units. Suitable monomers d) are unsubstituted N-vinyllactams and N-vinyllactam derivatives which may have, for example, one or more $C_1$-$C_6$-alkyl substituents, such as methyl, ethyl, n-propyl, isopropyl, n-butyl, sec-butyl, tert-butyl, etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam, etc. N-Vinylpyrrolidone and N-vinylcaprolactam are preferably used.

The novel copolymers preferably comprise up to 85, particularly preferably up to 60, in particular up to 50% by weight, based on the total weight of the monomers used for the polymerization, of at least one N-vinyllactam d) incorporated in the form of polymerized units. If a monomer d) is used, then it is preferably used in an amount of at least 1, particularly preferably at least 5, in particular at least 10% by weight.

Monomer e)

The novel copolymers may additionally comprise at least one monomer e) differing from the components a) to d), copolymerizable therewith and incorporated in the form of polymerized units.

The component e) is preferably selected from esters, differing from component a), of α,β-ethylenically unsaturated mono- and dicarboxylic acids with $C_1$-$C_{30}$-alkanols and $C_1$-$C_{30}$-alkanediols, amides of α,β-ethylenically unsaturated mono- and dicarboxylic acids with $C_2$-$C_{30}$-amino alcohols which have a primary or secondary amino group, N-vinylamides of saturated monocarboxylic acids, primary amides of α,β-ethylenically unsaturated monocarboxylic acids and the N-alkyl and N,N-dialkyl derivatives thereof, esters of vinyl alcohol and allyl alcohol with $C_1$-$C_{30}$-monocarboxylic acids, vinyl ethers, vinylaromatics, vinyl halides, vinylidene halides, $C_1$-$C_8$-monoolefins, nonaromatic hydrocarbons having at least two conjugated double bonds and mixtures thereof.

N-Vinylamide compounds suitable as monomers e) are, for example, N-vinyl-formamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide.

Suitable additional monomers e) are furthermore acrylamide, methacrylamide, N-methyl(meth)acrylamide, N-ethyl (meth)acrylamide, N-propyl(meth)acrylamide, N-(n-butyl) (meth)acrylamide, N-(tert-butyl)(meth)acrylamide, N,N-dimethyl(meth)acrylamide, N,N-diethyl(meth)acrylamide, piperidinyl(meth)acrylamide and (meth)acryloyl-morpholine.

Suitable additional monomers e) are furthermore 2-hydroxyethyl acrylate, 2-hydroxy-ethyl methacrylate, 2-hydroxyethyl ethacrylate, 2-hydroxypropyl acrylate, 2-hydroxy-propyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable additional monomers e) are furthermore 2-hydroxyethylacrylamide, 2-hydroxyethylmethacrylamide, 2-hydroxyethylethacrylamide, 2-hydroxypropyl-acrylamide, 2-hydroxypropylmethacrylamide, 3-hydroxypropylacrylamide, 3-hydroxy-propylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Suitable monomers e) are also polyetheracrylates, which are understood in the context of this invention as meaning generally esters of α,β-ethylenically unsaturated mono- and dicarboxylic acids with polyetherols. Suitable polyetherols are linear or branched substances which have terminal hydroxyl groups and comprise ether bonds. In general, they have a molecular weight of from about 150 to 20 000. Suitable polyetherols are polyalkylene glycols, such as polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers may comprise the alkylene oxide units randomly distributed or incorporated in the form of polymerized blocks. Ethylene oxide/propylene oxide copolymers are preferred.

Preferred components e) are polyetheracrylates of the formula II

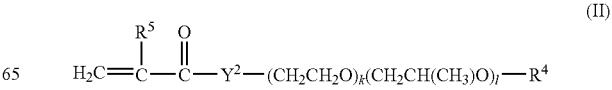

where
the sequence of the alkylene oxide units is arbitrary,
k and l, independently of one another, are an integer from 0 to 1000, the sum of k and l being at least 5,
$R^4$ is hydrogen, $C_1$-$C_{30}$-alkyl or $C_5$-$C_8$-cycloalkyl,
$R^5$ is hydrogen or $C_1$-$C_8$-alkyl and
$Y^2$ is O or $NR^6$, where $R^6$ is hydrogen, $C_1$-$C_{30}$-alkyl or $C_5$-$C_8$-cycloalkyl.

k is preferably an integer from 1 to 500, in particular from 3 to 250. Preferably, l is an integer from 0 to 100.

Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl.

Preferably, $R^4$ in the formula II is hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Preferably, $Y^2$ in the formula II is O or NH.

Suitable polyetheracrylates e) are, for example, the polycondensation products of the abovementioned α,β-ethylenically unsaturated mono- and/or dicarboxylic acids and the acid chlorides, acid amides and anhydrides thereof with polyetherols. Suitable polyetherols can easily be prepared by reacting ethylene oxide, 1,2-propylene oxide and/or epichlorohydrin with an initiator molecule, such as water or a short-chain alcohol $R^4$—OH. The alkylene oxides may be used individually, alternately in succession or as a mixture. The polyetheracrylates e) can be used alone or as mixtures for the preparation of the polymers used according to the invention.

Suitable additional monomers e) are methyl (meth)acrylate, methyl ethacrylate, ethyl (meth)acrylate, ethyl ethacrylate, n-butyl (meth)acrylate, tert-butyl methacrylate, tert-butyl ethacrylate, n-octyl (meth)acryl ate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate and mixtures thereof. Preferred monomers e) are the esters of α,β-ethylenically unsaturated mono- and dicarboxylic acids with $C_1$-$C_4$-alkanols.

Suitable additional monomers e) are furthermore N-(n-octyl)(meth)acrylamide, N-(tert-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)-(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth)acrylamide, N-nonadecyl(meth)acrylamide, N-arrachinyl-(meth)acrylamide, N-behenyl(meth)acrylamide, N-lignocerenyl(meth)acrylamide, N-cerotinyl(meth)acrylamide, N-melissinyl(meth)acrylamide, N-palmitoleinyl-(meth)acrylamide, N-oleyl(meth)acrylamide, N-linolyl(meth)acrylamide, N-linolenyl(meth)acrylamide, N-stearyl(meth)acrylamide and N-lauryl(meth)acrylamide.

Suitable additional monomers e) are furthermore vinyl acetate, vinyl propionate, vinyl butyrate and mixtures thereof.

Suitable additional monomers e) are furthermore ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The abovementioned additional monomers e) can be used individually or in the form of any desired mixtures.

The copolymers according to the invention preferably comprise at least one compound e), incorporated in the form of polymerized units, which is selected from $C_1$-$C_3$-alkyl methacrylates, hydroxy-$C_1$-$C_3$-alkyl methacrylates and mixtures thereof. Ethyl methacrylate, hydroxyethyl methacrylate and mixtures thereof are particularly preferred. In particular, ethyl methacrylate is used. The copolymers according to the invention preferably comprise these monomers, incorporated in the form of polymerized units, in an amount of not more than 50% by weight, particularly preferably not more than 45% by weight, based on the total weight of compounds of component a) and these compounds e).

The novel copolymers preferably comprise up to 25, particularly preferably up to 20, in particular up to 15% by weight, based on the total weight of the monomers used for the polymerization, of at least one monomer e) incorporated in the form of polymerized units. If a monomer e) is used, it is preferably used in an amount of at least 0.1, particularly preferably at least 1, in particular at least 5% by weight.

Crosslinking Agents f)

The novel copolymers can, if desired, comprise at least one crosslinking agent, i.e. a compound having two or more than two ethylenically unsaturated, nonconjugated double bonds incorporated in the form of polymerized units.

Preferably, crosslinking agents in an amount of from 0.01 to 3, particularly preferably from 0.1 to 2% by weight, based on the total weight of the monomers used for the polymerization, are used.

Suitable crosslinking agents f) are, for example, acrylic esters, methacrylic esters, allyl ethers or vinyl ethers of at least dihydric alcohols. Some or all of the OH groups of the parent alcohols may be etherified or esterified; however, the crosslinking agents comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentylglycol, 3-methylpentane-1,5-diol, 2,5-dimethyl-1,3-hexanediol, 2,4,4-trimethyl-1,3-pentanediol, 1,2-cyclohexanediol, 1,4-cyclohexanediol, 1-4-bis (hydroxymethyl)cyclohexane, the monoester of neopentylglycol with hydroxypivalic acid, 2,2-bis(4-hydroxyphenyl)-propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol and polyethylene glycols, polypropylene glycols and polytetrahydrofurans having molecular weights of in each case from 200 to 10 000. In addition to the homopolymers of ethylene oxide or of propylene oxide, block copolymers of ethylene oxide or propylene oxide or copolymers which comprise incorporated ethylene oxide and propylene oxide groups may also be used. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose and mannose. Of course, the polyhydric alcohols can also be used after reaction with ethylene oxide and propylene oxide, in the form of the corresponding ethoxylates or propoxylates. The polyhydric alcohols can also first be converted into the corresponding glycidyl ethers by reaction with epichlorohydrin.

Further suitable crosslinking agents f) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamic alcohol, citronellol, crotyl alcohol or cis-9-octadecen-1-ol. However, the monohydric, unsaturated alcohols may also be esterified with polybasic carboxylic acids, for example malonic acid, tartaric acid, trimellitic acid, phthalic acid, terephthalic acid, citric acid or succinic acid.

Further suitable crosslinking agents f) are esters of unsaturated carboxylic acids with the polyhydric alcohols described above, for example of oleic acid, crotonic acid, cinnamic acid or 10-undecenoic acid.

Further suitable crosslinking agents f) are urethane diacrylates and urethane polyacrylates, as commercially available, for example, under the name Laromer®.

Other suitable crosslinking agents f) are straight-chain or branched, linear or cyclic, aliphatic or aromatic hydrocarbons which have at least two double bonds which, in the case of aliphatic hydrocarbons, may be nonconjugated, e.g. divinylbenzene, divinyltoluene, 1,7-octadiene, 1,9-decadiene, 4-vinyl-1-cyclohexene, trivinylcycohexane or polybutadienes having molecular weights of from 200 to 20 000.

Further suitable crosslinking agents f) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Also suitable are the amides of allylamine and unsaturated carboxylic acids, such as acrylic acid, methacrylic acid, itaconic acid, maleic acid or at least dibasic dicarboxylic acids, as described above.

Furthermore, triallylamine and triallylmonoalkylammonium salts, e.g. triallylmethylammonium chloride or methylsulfate, are suitable as crosslinking agents f).

N-Vinyl compounds of urea derivatives, at least difunctional amides, cyanurates or urethanes, for example of urea, ethyleneurea, propyleneurea or tartaramide, e.g. N,N'-divinylethyleneurea or N,N'-divinylpropyleneurea, are also suitable.

Further suitable crosslinking agents f) are divinyldioxane, tetraallylsilane or tetravinylsilane.

Of course, mixtures of the abovementioned compounds f) may also be used. Water-soluble crosslinking agents f) are preferably used.

Particularly preferably used crosslinking agents f) are, for example, methylenebisacrylamide, triallylamine and triallylalkylammonium salts, divinylimidazole, pentaerythrityl triallyl ether, N,N'-divinylethyleneurea, reaction products of polyhydric alcohols with acrylic acid or methacrylic acid, methacrylates and acrylates of polyalkylene oxides or polyhydric alcohols which have been reacted with ethylene oxide and/or propylene oxide and/or epichlorohydrin.

Very particularly preferred crosslinking agents f) are pentaerythrityl triallyl ether, methylenebisacrylamide, N,N'-divinylethyleneurea, triallylamine and triallylmonoalkylammonium salts and acrylates of glycol, butanediol, trimethylolpropane or glycerol or acrylates of glycol, butanediol, trimethylolpropane or glycerol which has been reacted with ethylene oxide and/or epichlorohydrin.

Preferred copolymers are those which comprise
from 20 to 90, particularly preferably from 25 to 85% by weight of at least one compound a),
from 5 to 40, particularly preferably from 10 to 35, in particular from 13 to 30% by weight of acrylic acid and/or methacrylic acid b),
from 0.5 to 25, particularly preferably from 1 to 20, in particular from 2 to 16% by weight of a monomer composition c),
from 0 to 85, particularly preferably from 1 to 60, in particular from 5 to 50% by weight of at least one compound d),
from 0 to 25, particularly preferably from 0.1 to 20, in particular from 1 to 15% by weight of at least one compound e),
from 0 to 5, particularly preferably from 0.01 to 3, in particular from 0.1 to 2% by weight of at least one compound f),
incorporated in the form of polymerized units.

A preferred embodiment comprises copolymers which consist of repeating units of
tert-butyl acrylate,
acrylic acid and/or methacrylic acid,
N-(tert-butyl)aminoethyl (meth)acrylate or
N-[3-(dimethylamino)propyl]methacrylamide or
N,N-dimethylaminoethyl methacrylate or N-vinylimidazole.

A further preferred embodiment comprises copolymers which consist of repeating units of
tert-butyl acrylate,
tert-butyl methacrylate,
acrylic acid and/or methacrylic acid
N-(tert-butyl)aminoethyl (meth)acrylate or
N-[3-(dimethylamino)propyl]methacrylamide or
N,N-dimethylaminoethyl methacrylate or N-vinylimidazole.

A further preferred embodiment comprises copolymers which consist of repeating units of
tert-butyl acrylate,
acrylic acid and/or methacrylic acid,
N-(tert-butyl)acrylamide and
N-(tert-butyl)aminoethyl (meth)acrylate or
N-[3-(dimethylamino)propyl]methacrylamide or
N,N-dimethylaminoethyl methacrylate or N-vinylimidazole.

A further preferred embodiment comprises copolymers which consist of repeating units of
tert-butyl acrylate,
acrylic acid and/or methacrylic acid,
vinylpyrrolidone and
N-(tert-butyl)aminoethyl (meth)acrylate or
N-[3-(dimethylamino)propyl]methacrylamide or
N,N-dimethylaminoethyl methacrylate or N-vinylimidazole.

A further preferred embodiment comprises copolymers which consist of repeating units of
tert-butyl acrylate,
acrylic acid and/or methacrylic acid,
N-(tert-butyl)acrylamide,
vinylpyrrolidone and
N-(tert-butyl)aminoethyl (meth)acrylate or
N-[3-(dimethylamino)propyl]methacrylamide or
N,N-dimethylaminoethyl methacrylate or N-vinylimidazole.

Copolymers which comprise, incorporated in the form of polymerized units,
a) tert-butyl acrylate,
b) acrylic acid and/or methacrylic acid, c) N-(tert-butyl)aminoethyl acrylate or N-(tert-butyl)aminoethyl (meth)acrylate or N-[3-(dimethylamino)propyl] methacrylamide or N,N-dimethylaminoethyl methacrylate or N-vinylimidazole,
d) if appropriate, vinylpyrrolidone and
e) at least one compound which is selected from $C_1$-$C_3$-alkyl methacrylates, hydroxy-$C_1$-$C_3$-alkyl methacrylates and mixtures thereof, with the proviso that the proportion by weight of component a) is equal to or greater than the proportion by weight of component e), are also preferred.

A particularly preferred embodiment comprises copolymers which consist of repeating units of tert-butyl acrylate,
acrylic acid and/or methacrylic acid,
N-(tert-butyl)aminoethyl (meth)acrylate or N-vinylimidazole and
ethyl methacrylate, with the proviso that the proportion by weight of tert-butyl acrylate is equal to or greater than the proportion by weight of ethyl methacrylate.

A further preferred embodiment comprises copolymers which consist of repeating units of tert-butyl acrylate,
acrylic acid and/or methacrylic acid,
N-vinylpyrrolidone,
N-(tert-butyl)aminoethyl (meth)acrylate or N-vinylimidazole and
ethyl methacrylate, with the proviso that the proportion by weight of tert-butyl acrylate is equal to or greater than the proportion by weight of ethyl methacrylate.

Copolymers which comprise, based in each case on the total weight of the monomers used for the polymerization, from 20 to 80% by weight, preferably from 25 to 75% by weight, of tert-butyl acrylate and ethyl methacrylate, with the proviso that the proportion by weight of tert-butyl acrylate is equal to or greater than the proportion by weight of ethyl methacrylate,
from 5 to 30% by weight, preferably from 10 to 25% by weight, of acrylic acid and/or methacrylic acid,
from 1 to 20% by weight, preferably from 3 to 15% by weight, of a monomer composition comprising methacrylic acid and N-vinylimidazole or N-(tert-butyl)aminoethyl (meth)acrylate and
from 0 to 35% by weight of vinylpyrrolidone, incorporated in the form of polymerized units are also preferred.

The preparation of the novel copolymers can be effected, for example, by solution, precipitation, suspension or emulsion polymerization. Such methods are known in principle to a person skilled in the art. The preparation by solution polymerization is preferred.

According to the invention, a monomer composition c) which comprises c1) at least one compound having an $\alpha,\beta$-ethylenically unsaturated double bond capable of free radical polymerization and at least one anionogenic and/or anionic group per molecule and
c2) at least one compound having an $\alpha,\beta$-ethylenically unsaturated double bond capable of free radical polymerization and at least one cationogenic and/or cationic group per molecule is used for the preparation of the copolymers, the molar ratio of anionogenic and anionic groups of the component c1) to cationogenic and cationic groups of the component c2) being about 1:1.

The invention therefore furthermore relates to a process for the preparation of an ampholytic polymer which comprises a molar excess of anionogenic and/or anionic groups, in which i) a monomer composition c) which comprises
c1) at least one compound having an $\alpha,\beta$-ethylenically unsaturated double bond capable of free radical polymerization and at least one anionogenic and/or anionic group per molecule and
c2) at least one compound having an $\alpha,\beta$-ethylenically unsaturated double bond capable of free radical polymerization and at least one cationogenic and/or cationic group per molecule is provided, the molar ratio of anionogenic and anionic groups of the component c1) to cationogenic and cationic groups of the component c2) being about 1:1, and ii) the monomer composition c) is copolymerized in a reaction zone with
a) at least one branched $C_3$- to $C_5$-alkyl acrylate,
b) acrylic acid and/or methacrylic acid
and, if appropriate, further compounds copolymerizable therewith.

Regarding the components used for the copolymerization, reference is made to the preceding statements on suitable and preferred components of the novel copolymers.

Preferred solvents for the polymerization of aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of the dihydric alcohols, diethylene glycol, triethylene glycol, polyethylene glycols having number average molecular weights of up to about 3000, glycerol and dioxane. The polymerization in water or in a water/alcohol mixture, for example in a water/ethanol mixture, is particularly preferred.

The polymerization can be effected in principle at the pH produced by the monomers used. If at least one N-vinyllactam is used for the polymerization (=component d)), the pH of the polymerization medium is preferably brought to a value of from 5 to 8, preferably from 6 to 7. It is then advantageous to keep the pH in this range during the polymerization. All inorganic or organic bases (and, if appropriate, acids), in particular those which, apart from any salt formation, undergo no reaction with the monomers, are in principle suitable for establishing the pH before, during or after the polymerization. Suitable bases are, for example, alkali metal and alkaline earth metal hydroxides, tertiary amines, such as triethylamine, and amino alcohols, such as triethanolamine, methyldiethanolamine or dimethylethanolamine. At least one tertiary amine which is selected in particular from N,N-dimethylethanolamine, N-methyl-diethanolamine, triethanolamine and mixtures thereof is preferably used for establishing the pH. If at least one N-vinyllactam (=component d)) is used for the polymerization, the pH of the polymerization medium is preferably established with N,N-dimethylethanolamine.

The polymerization temperatures are preferably from about 30 to 120° C., particularly preferably from 40 to 100° C. The polymerization is usually effected under atmospheric pressure but may also take place under reduced or superatmospheric pressure. A suitable pressure range is from 1 to 5 bar.

For the copolymerization, the monomers can be polymerized with the aid of free radical initiators.

Initiators which may be used for the free radical polymerization are the peroxo and/or azo compounds customary for this purpose, for example alkali metal or ammonium peroxodisulfates, diacetyl peroxide, dibenzoyl peroxide, succinyl peroxide, di-tert-butyl peroxide, tert-butyl perbenzoate, tert-butyl perpivalate, tert-butyl peroxy-2-ethyl-hexanoate, tert-butyl permaleate, cumyl hydroperoxide, diisopropyl peroxodicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-amidinopropane) hydrochloride (V50 from Wako Pure Chemicals Industries, Ltd.), or 2,2'-azobis(2-methylbutyronitrile). Initiator mixtures or redox initiator systems, e.g. ascorbic acid/iron(II) sulfate/sodium peroxodisulfate, tert-butyl hydroperoxide/sodium disulfite, tert-butyl hydroxperoxide/sodium hydroxymethanesulfinate, $H_2O_2/Cu^I$, are also suitable.

For establishing the molecular weight, the polymerization can be effected in the presence of at least one regulator. Regulators which may be used are the conventional compounds known to a person skilled in the art, such as sulfur compounds, e.g. mercaptoethanol, 2-ethylhexyl thioglycolate, thioglycolic acid or dodecyl mercaptan, and tribromochloromethane or other compounds which have a regulating effect on the molecular weight of the polymers obtained. A preferred regulator is cysteine.

For obtaining very pure polymers having a low residual monomer content, the polymerization (main polymerization) may be followed by a postpolymerization step. The postpolymerization can be effected in the presence of the same initiator system as the main polymerization or of another initiator system. The postpolymerization is preferably effected at least at the same temperature as the main polymerization but preferably at a higher temperature than the main polymerization. If desired, the reaction batch can be subjected to stripping with steam or to a steam distillation after the polymerization or between the first and the second polymerization step.

If an organic solvent is used in the preparation of the polymers, this can be removed by conventional methods known to a person skilled in the art, for example by distillation under reduced pressure.

The liquid polymer compositions obtained can be converted into powder form by various drying methods, for example spray drying, fluidized spray drying, drum drying or freeze drying. Spray drying is preferably used. The dry polymer powders thus obtained can advantageously be converted into an aqueous solution or dispersion again by dissolution or redispersing in water. Copolymer powders have the advantage of better storability and easier transportability and as a rule have less tendency to attack by germs.

Polymer Complex PE)

The invention furthermore relates to polyelectrolyte complexes which comprise at least one ampholytic copolymer as defined above and at least one polyelectrolyte PE) differing therefrom. Suitable polyelectrolytes PE) are selected from anionic, cationic and amphoteric polymers.

The polyelectrolyte complexes preferably comprise the ampholytic copolymer and the polymer PE) in a weight ratio of from about 50:1 to 1:50, particularly preferably from 20:1 to 1:20, in particular from 5:1 to 1:5.

The novel polyelectrolyte complexes preferably comprise at least one polymer PE) containing acid groups.

Suitable carboxyl-containing polymers PE) are obtainable, for example, by free radical polymerization of $\alpha,\beta$-ethylenically unsaturated monomers. Monomers pe.1) which comprise at least one $\alpha,\beta$-ethylenically unsaturated double bond capable of free radical polymerization and at least one anionogenic and/or anionic group per molecule are used.

Suitable carboxyl-containing polymers PE) are furthermore carboxyl-containing polyurethanes.

The monomers pe.1) are preferably selected from monoethylenically unsaturated carboxylic acids, sulfonic acids, phosphonic acids and mixtures thereof.

The monomers pe.1) include monoethylenically unsaturated mono- and dicarboxylic acids of 3 to 25, preferably 3 to 6, carbon atoms, which may also be used in the form of their salts or anhydrides. Examples of these are acrylic acid, methacrylic acid, ethacrylic acid, $\alpha$-chloroacrylic acid, crotonic acid, maleic acid, maleic anhydride, itaconic acid, citraconic acid, mesaconic acid, glutaconic acid, aconitic acid and fumaric acid. The monomers pe.1) furthermore include the monoesters of monoethylenically unsaturated dicarboxylic acids of 4 to 10, preferably 4 to 6, carbon atoms, for example of maleic acid, such as monomethyl maleate. The monomers pe.1) also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-2-methacryloyloxypropylsulfonic acid, styrenesulfonic acid, 2-acrylamido-2-methylpropanesulfonic acid, vinylphosphonic acid and allylphosphonic acid. The monomers pe.1) also include the salts of the abovementioned acids, in particular the sodium, potassium and ammonium salts and the salts with the abovementioned amines. The monomers pe.1) may be used as such or as mixtures with one another. Said amounts by weight are all based on the acid form.

The component pe.1) is preferably selected from acrylic acid, methacrylic acid, ethacrylic acid, $\alpha$-chloroacrylic acid, crotonic acid, maleic acid, maleic anhydride, fumaric acid, itaconic acid, citraconic acid, mesaconic acid, glutaconic acid, aconitic acid and mixtures thereof.

The component pe.1) is particularly preferably selected from acrylic acid, methacrylic acid and mixtures thereof.

The abovementioned monomers pe.1) may each be used individually or in the form of any desired mixtures.

In principle, suitable comonomers for the preparation of the polymers PE) containing acid groups are the compounds a) to f) mentioned above as components of the ampholytic copolymer, with the proviso that the mole fraction of anionogenic and anionic groups which the polymer PE) comprises incorporated in the form of polymerized units is greater than the mole fraction of cationogenic and cationic groups.

In a preferred embodiment, the polymers PE) comprise at least one monomer which is incorporated in the form of polymerized units and is selected from the abovementioned crosslinking agents f). Reference is made to suitable and preferred crosslinking agents f).

Anionic polymers preferred as polymer PE) are, for example, homo- and copolymers of acrylic acid and methacrylic acid and salts thereof. These also include crosslinked polymers of acrylic acid, as available under the INCI name Carbomer. Such crosslinked homopolymers of acrylic acid are, for example, commercially available under the name Carbopol® from BF GOODRICH. Hydrophobically modified crosslinked polyacrylate polymers, such as Carbopol® Ultrez 21 from Noveon, are also preferred.

Polyelectrolyte complexes based on homo- and copolymers of acrylic acid and methacrylic acid are suitable in an advantageous manner for formulation as gels, for example for hair setting gels, and for formulating foams.

Further examples of suitable anionic polymers are copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of (meth)acrylic acid and polyetheracrylates, the polyether chain being terminated by a $C_8$-$C_{30}$-alkyl radical. These include, for example, acrylate/beheneth-25 methacrylate copolymers, which are available under the name Aculyn® from Rohm und Haas. Particularly suitable polymers are furthermore copolymers of tert-butyl acrylate, ethyl acrylate, methacrylic acid (e.g. Luvimer® 100P), copolymers of ethyl acrylate and methacrylic acid (e.g. Luviumer® MAE), copolymers of N-tert-butylacrylamide, ethyl acrylate and acrylic acid (Ultrahold® 8, strong), copolymers of vinyl acetate, crotonic acid and, if appropriate, further vinyl esters (e.g. Luviset® brands), maleic anhydride copolymers, if appropriate reacted with alcohol, anionic polysiloxanes, e.g. carboxyl-functional, tert-butyl acrylate, methacrylic acid (e.g. Luviskol® VBM), copolymers of acrylic acid and methacrylic acid with hydrophobic monomers, such as $C_4$-$C_{30}$-alkyl esters of meth (acrylic acid), $C_4$-$C_{30}$-alkylvinyl esters, $C_4$-$C_{30}$-alkyl vinyl ethers and hyaluronic acid. Examples of anionic polymers are furthermore vinyl acetate/crotonic acid copolymers as are commercially available, for example, under the names Resyn® (National Starch) and Gafset® (GAF), and vinylpyrrolidone/vinyl acrylate copolymers, available, for example, under the trademark Luviflex® (BASF). Further suitable polymers are the vinylpyrrolidone/acrylate terpolymer available under the name Luviflex® VBM-35 (BASF) and sodium sulfonate-containing polyamides or sodium sulfonate-containing polyesters.

The group of the suitable anionic polymers furthermore comprises, by way of example, Balance® CR (National Starch; acrylate copolymer), Balance® 0/55 (National Starch; acrylate copolymer), Balance® 47 (National Starch; octylacrylamide/acrylate/butylaminoethyl methacrylate copolymer), Aquaflex® FX 64 (ISP; isobutylene/ethylmaleimide/hydroxyethylmaleimide copolymer), Aquaflex® SF-40 (ISP/National Starch; VP/vinyl caprolactam/DMAPA acrylate copolymer), Allianz® LT-120 (ISP/Rohm & Haas; acrylate/C1-2 succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxide/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylate copolymer), Aculyne® 258 (Rohm & Haas; acrylate/hydroxyester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), DynamX (National Starch; polyurethane-14 AMP-acrylates copolymer), Resyn XP (National Starch; acrylates/octylacrylamide copolymer), Fixomer A-30 (Ondeo Nalco; polymethacrylic acid (and) acrylamidoethylpropanesulfonic acid), Fixate G-100 (Noveon; AMP-acrylates/allyl methacrylate copolymer).

Suitable copolymers PE) are also the terpolymers described in U.S. Pat. No. 3,405,084 and obtained from vinylpyrrolidone, $C_1$-$C_{10}$-alkyl, cycloalkyl and aryl (meth)acrylates and acrylic acid. Suitable copolymers PE) are furthermore the terpolymers described in EP-A-0 257 444 and EP-A-0 480 280 and obtained from vinylpyrrolidone, tert-butyl (meth)acrylate and (meth)acrylic acid. Suitable copolymers PE) are furthermore the copolymers described in DE-A-42 23 066 and comprising, incorporated in the form of polymerized units, at least one (meth)acrylate, (meth)acrylic acid and N-vinylpyrrolidone and/or N-vinylcaprolactam. The disclosure of these documents is hereby incorporated by reference.

Suitable carboxyl-containing polymers PE) are furthermore carboxyl-containing polyurethanes.

EP-A-636361 discloses suitable block copolymers having polysiloxane blocks and polyurethane/polyurea blocks, which have carboxyl and/or sulfo groups. Suitable silicone-containing polyurethanes are also described in WO 97/25021 and EP-A-751 162. Suitable polyurethanes are also described in DE-A42 25 045, which is hereby incorporated by reference in its entirety. These polyurethanes are in principle composed of i) at least one compound which comprises two or more active hydrogen atoms per molecule,
ii) at least one carboxyl-comprising diol or a salt thereof and
iii) at least one polyisocyanate.

Component i) comprises, for example, diols, diamines, amino alcohol and mixtures thereof. The molecular weight of these compounds is preferably from about 56 to 280. If desired, up to 3 mol % of said compounds may be replaced by triols or triamines.

Usable diols i) are, for example, ethylene glycol, propylene glycol, butylene glycol, neopentylglycol, cyclohexanedimethylol, di-, tri-, tetra-, penta- or hexaethylene glycol and mixtures thereof. Neopentylglycol and/or cyclohexanedimethylol are preferably used. Suitable amino alcohols i) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol, etc. Suitable diamines i) are, for example, ethylenediamine, propylenediamine, 1,4-diaminobutane, 1,5-diaminopentane and 1,6-diaminohexane and $\alpha,\omega$-diaminopolyethers which can be prepared by aminating polyalkylene oxides with ammonia.

The component i) may also be a polymer having a number average molecular weight of from about 300 to 5000, preferably from about 400 to 4000, in particular from 500 to 3000. Useable polymers i) are, for example, polyesterdiols, polyetherdiols and mixtures thereof. Polyetherols are, preferably, polyalkylene glycols, e.g. polyethylene glycols, polypropylene glycols, polytetrahydrofurans, etc., block copolymers of ethylene oxide and propylene oxide or block copolymers of ethylene oxide, propylene oxide and butylene oxide, which comprise the alkylene oxide units incorporated in the form of randomly distributed polymerized units or in the form of blocks. Suitable polytetrahydrofurans i) can be prepared by cationic polymerization of tetrahydrofuran in the presence of acidic catalysts, e.g. sulfuric acid or fluorosulfuric acid. Such preparation processes are known to a person skilled in the art. Useable polyesterdiols i) preferably have a number average molecular weight of from about 400 to 5000, preferably from 500 to 3000, in particular from 600 to 2000. Suitable polyesterdiols i) are all those which are usually used for the preparation of polyurethanes, in particular those based on aromatic dicarboxylic acids, such as terephthalic acid, isophthalic acid, phthalic acid, sodium or potassium salts of sulfoisophthalic acid, etc., aliphatic dicarboxylic acids, such as adipic acid or succinic acid, etc., and cycloaliphatic dicarboxylic acids, such as 1,2-, 1,3- or 1,4-cyclohexanedicarboxylic acid. Particularly suitable diols are aliphatic diols, such as ethylene glycol, propylene glycol, 1,6-hexanediol, neopentylglycol, diethylene glycol, polyethylene glycols, polypropylene glycols, 1,4-dimethylolcyclohexane, etc.

Suitable compounds ii) which have two active hydrogen atoms and at least one carboxyl group per molecule are, for example, dimethylolpropanoic acid and mixtures which comprise dimethylolpropanoic acid.

The component iii) comprises conventional aliphatic, cycloaliphatic and/or aromatic polyisocyanates, such as tetramethylene diisocyanate, hexamethylene diisocyanate, methylenediphenyl diisocyanate, toluene 2,4- and 2,6-diisocyanate and the isomer mixtures thereof, o- and m-xylene diisocyanate, 1,5-naphthylene diisocyanate, 1,4-cyclohexylene diisocyanate, dicyclohexylmethane diisocyanate and mixtures thereof, in particular isophorone diisocyanate and/or dicyclohexylmethane diisocyanate. If desired, up to 3 mol % of said compounds may be replaced by triisocyanates.

Suitable polymers PE) are furthermore cationic polymers. These include, for example, polymers having the name Polyquaternium according to INCI, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamido copolymers (polyquaternium-7) and chitosan. Suitable cationic (quaternized) polymers are also Merquat® (polymer based on dimethyldiallylammonium chloride), Gafquat® (quaternary polymers which are formed by reaction of polyvinylpyrrolidone with quaternary ammonium compounds), polymer JR (hydroxyethylcellulose having cationic groups) and plant-based cationic polymers, e.g. guar polymers, such as the Jaguar® brands from Rhodia.

Suitable polymers PE) are also amphoteric or zwitterionic polymers, such as the octylacrylamide/methyl methacrylate/tert-butylaminoethyl methacrylate/2-hydroxypropyl methacrylate copolymers obtainable under the name Amphomer® (National Starch) and zwitterionic polymers as disclosed, for example, in German Patent Applications DE 39 29 973, DE 21 50 557, DE 28 17 369 and DE 37 08 451. Acrylamidopropyltrimethylammonium chloride/acrylic acid or methacrylic acid copolymers and the alkali metal and ammonium salts thereof are preferred zwitterionic polymers. Further suitable zwitterionic polymers are methacryloylethylbetaine/methacrylate copolymers which are commercially available under the name Amersette® (AMERCHOL) and copolymers of hydroxyethyl methacrylate, methyl methacrylate, N,N-dimethylaminoethyl methacrylate and acrylic acid (Jordapon®).

The ampholytic copolymers and polyelectrolyte complexes described above are very useful for the preparation of cosmetic and pharmaceutical compositions. They serve, for example, as polymeric film formers in formulations for personal hygiene, which includes applications in cosmetic formulations for keratinous surfaces, such as skin, hair, and nails, and also oral hygiene preparations. They can be used and formulated in a very wide range of cosmetic formulations and are compatible with the conventional components. The novel ampholytic copolymers and polyelectrolyte complexes are particularly suitable for the preparation of cosmetic hair compositions. Compared with conventional polymers known from the prior art, they are advantageously suitable for the production of elastic hairstyles in combination with strong setting (even at high atmospheric humidity). The novel ampholytic copolymers and polyelectrolyte complexes also have good compatibility with propellants, good solubility in water or aqueous/alcoholic solvent mixtures and suitability for use in low-VOC formulations and can be readily washed out. In addition, they also generally have good conditioning properties, i.e. they improve hair treated therewith in its sensory properties, such as handle, body, handleability, etc.

Cosmetically Acceptable Carriers B)

The novel compositions comprise a cosmetically or pharmaceutically acceptable carrier B) which is selected from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with monohydric, dihydric or trihydric alcohols, which esters differ from iii),
v) saturated acyclic and cyclic hydrocarbons,
vi) fatty acids,
vii) fatty alcohols,
viii) propellants
and mixtures thereof.

The novel compositions comprise, for example, an oil or fat component B) which is selected from: hydrocarbons of low polarity, such as mineral oils; linear saturated hydrocarbons, preferably of more than 8 carbon atoms, such as tetradecane, hexadecane, octadecane, etc.; cyclic hydrocarbons, such as decahydronaphthalene; branched hydrocarbons; animal and vegetable oils; waxes; wax esters; vaseline; esters, preferably esters of fatty acids, such as the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkylbenzoates, benzyl benzoate; other cosmetic esters, such as fatty acid triglycerides, propylene glycol monolaurate, polyethylene glycol monolaurate, $C_{10}$-$C_{15}$-alkyl lactates, etc., and mixtures thereof.

Suitable silicone oils B) are, for example, linear polydimethylsiloxanes, poly(methylphenylsiloxanes), cyclic siloxanes and mixtures thereof. The number average molecular weight of the polydimethylsiloxanes and poly(methylphenylsiloxanes) is preferably from about 1000 to 150 000 g/mol. Preferred cyclic siloxanes have 4- to 8-membered rings. Suitable cyclic siloxanes are commercially available, for example, under the name cyclomethicone.

Preferred oil or fat components B) are selected from paraffin and liquid paraffins; vaseline; natural fats and oils, such as castor oil, soybean oil, peanut oil, olive oil, sunflower oil, sesame oil, avocado oil, cocoa butter, almond oil, peach kernel oil, cod liver oil, lard, spermaceti, sperm oil, wheat germ oil, macadamia nut oil, evening primrose oil, jojoba oil; fatty alcohols, such as lauryl alcohol, myristyl alcohol, cetyl alcohol, stearyl alcohol, oleyl alcohol; fatty acids, such as myristic acid, stearic acid, palmitic acid, oleic acid, linoleic acid, linolenic acid and various saturated, unsaturated and substituted fatty acids thereof; waxes, such as beeswax, carnauba wax, candililla wax, spermaceti and mixtures of the above-mentioned oil and fat components.

Suitable cosmetically and pharmaceutically compatible oil or fat components B) are described in Karl-Heinz Schrader, Grundlagen und Rezepturen der Kosmetika, 2nd Edition, Verlag Hüthig, Heidelberg, pages 319-355, which is hereby incorporated by reference.

Suitable hydrophilic carriers B) are selected from water and monohydric, dihydric or polyhydric alcohols of, preferably, 1 to 8 carbon atoms, such as ethanol, n-propanol, isopropanol, propylene glycol, glycerol, sorbitol, etc.

The novel cosmetic compositions may be cosmetic skin compositions, cosmetic hair compositions or dermatological, hygiene or pharmaceutical compositions. Owing to their film-forming properties, the copolymers and polyelectrolyte complexes described above are particularly suitable as additives for hair and skin cosmetics.

The novel compositions are preferably in the form of a gel, foam, spray, ointment, cream, emulsion, suspension, lotion, milk or paste. If desired, liposomes or microspheres may also be used.

The novel cosmetically or pharmaceutically active compositions may additionally comprise cosmetically and/or dermatologically active substances and assistants. The novel cosmetic compositions preferably comprise at least one copolymer and/or one polyelectrolyte complex as defined above (=component A), at least one carrier B) as defined above and at least one component which differs therefrom and is selected from cosmetically active substances, emulsifiers, surfactants, preservatives, perfume oils, thickeners, hair polymers, hair and skin conditioners, graft polymers, water-soluble or dispersible silicone-containing polymers, light stabilizers, bleaches, gel formers, care compositions, colorants, tinting compositions, tanning compositions, dyes, pigments, consistency agents, moisturizers, refatting agents, collagen, protein hydrolysis products, lipids, antioxidants, antifoams, antistatic agents, emollients and softeners.

Conventional thickeners in such formulations are crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Nonionic thickeners are preferably used.

Suitable cosmetically and/or dermatologically active substances are, for example, color-imparting active substances, skin and hair pigmenting compositions, tinting compositions, tanning compositions, bleaches, keratin-hardening substances, antimicrobial active substances, light filter active substances, repellent active substances, substances having a hyperemic effect, keratolytic and keratoplastic substances, antidandruff active substances, antiphlogistic compositions, substances having a keratinizing effect, antioxidants or active substances acting as free radical scavengers, substances which moisturize skin or keep it moist, refatting active substances, antierythematous or antiallergic active substances, and mixtures thereof.

Active substances which produce an artificial tan and are suitable for tanning the skin without natural or artificial exposure to UV rays are, for example, dihydroxyacetone, alloxane and walnut shell extract. Suitable keratin-hardening substances are as a rule active substances as are also used in antiperspirants, for example potassium aluminum sulfate, aluminum hydrochloride, aluminum lactate, etc. Antimicrobial active substances are used for destroying microorganisms or for inhibiting their growth and therefore serve both as a preservative and as a deodorant which reduces the formation or the intensity of body odor. These include, for example, conventional preservatives known to a person skilled in the art, such as p-hydroxybenzoic esters, imidazolidinylurea, formaldehyde, sorbic acid, benzoic acid, salicylic acid, etc. Such deodorants are, for example, zinc ricinoleate, triclosan, alkylolamides of undecylenoic acid, triethyl citrate, chlorhexidine, etc. Suitable air filter active substances are substances which absorb UV rays in the UV-B and/or UV-A range. Suitable UV filters are, for example, 2,4,6-triaryl-1,3,5-triazines in which the aryl groups may each carry at least one substituent which is preferably selected from hydroxyl, alkoxy, especially methoxy, alkoxycarbonyl, especially methoxycarbonyl and ethoxycarbonyl, and mixtures thereof. p-Aminobenzoic esters, cinnamic esters, benzophenones, camphor derivatives and pigments which provide screening from UV rays, such as titanium dioxide, talc and zinc oxide, are furthermore suitable. Suitable repellent active substances are compounds which are capable of keeping certain animals, in particular insects, away from humans or for repelling them. These include, for example, 2-ethyl-1,3-hexanediol, N,N-diethyl-m-toluamide, etc. Suitable substances which have a hyperemic effect and stimulate the blood flow of the skin are, for example, essential oils, such as dwarf pine-needle oil, lavender, rosemary, juniper, horse chestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active substances are, for example, sulfur, sulfopolyethylene glycol sorbitan monooleate, sulforicinol polyethoxylate, pyrithione zinc, pyrithione aluminum, etc. Suitable antiphlogistic agents which counteract skin irritation are, for example, allantoin, bisabolol, dragosantol, camomile extract, panthenol, etc.

The novel cosmetic compositions may comprise, as cosmetic and/or pharmaceutical active substance (as well as, if appropriate, as assistant), at least one cosmetically or pharmaceutically acceptable polymer which differs from the novel ampholytic copolymers and the polymers which form the novel polyelectrolyte complexes. These include very generally neutral polymers.

Suitable neutral polymers are, for example, polyvinylpyrrolidone, copolymers of N-vinylpyrrolidone and vinyl acetate and/or vinyl propionate, polysiloxanes, polyvinylcaprolactam and other copolymers with N-vinylpyrrolidone, polyethylenimines and salts thereof, polyvinylamines and salts thereof, cellulose derivatives, polyaspartic acid salts and derivatives. These include, for example, Luviflex® Swing (partly hydrolyzed copolymer of polyvinyl acetate and polyethylene glycol, from BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, for example based on itaconic acid and aliphatic diamines, as described, for example, in DE-A43 33 238.

Suitable polymers are also nonionic, siloxane-containing, water-soluble or water-dispersible polymers, e.g. polyethersiloxanes, such as Tegopren® (from Goldschmidt) or Belsil® (from Wacker).

The formulation base of novel pharmaceutical compositions preferably comprises pharmaceutically acceptable excipients. Pharmaceutically acceptable are the excipients which are known to be useable in pharmacy, food technology and ancillary areas, in particular those listed in relevant pharmacopeias (e.g. DAB, Ph. Eur., BP, NF) and other excipients whose properties make them suitable for physiological use.

Suitable excipients may be: lubricants, wetting agents, emulsifying and suspending media, preservatives, antioxidants, anti-irritant substances, chelating agents, emulsion stabilizers, film formers, gel formers, odor masking compositions, resins, hydrocolloids, solvents, solubilizers, neutralizing agents, permeation accelerators, pigments, quaternary ammonium compounds, refatting and overfatting compositions, ointment, cream and oil bases, silicone derivatives, stabilizers, sterilizers, propellants, drying agents, opacifiers, thickeners, waxes, softeners and white oils. A relevant embodiment is based on the knowledge of a person skilled in the art, as described, for example, in Fielder, H. P., Lexikon der Hilfsstoffe für Pharmazie, Kosmetik und angrenzende Gebiete, 4th Edition, Aulendorf: ECV-Editio-Kantor-Verlag, 1996.

For the preparation of the novel dermatological compositions, the active substances can be mixed or diluted with a suitable excipient. Excipients may be solid, semisolid or liquid materials which may serve as a vehicle, carrier or medium for the active substance. The admixing of further excipients is effected, if desired, in a manner known to a person skilled in the art. Furthermore, the polymers and polyelectrolyte complexes are suitable as excipients in pharmacy, preferably as or in coating material(s) or binder(s) for solid dosage forms. They can also be used in creams and as tablet coating materials and tablet binders.

According to a preferred embodiment, the novel compositions are skin cleansing compositions.

Preferred skin cleansing compositions are soaps of liquid to gel-like consistency, such as transparent soaps, luxury soaps, deodorant soaps, cream soaps, baby soaps, skin protection soaps, abrasive soaps and syndets, pasty soaps, spreading soaps and wax pastes, liquid wash, shower and bath preparations, such as wash lotions, shower baths and gels, foam baths, oil baths and scrubbing preparations, and shaving foams, lotions and creams.

According to a further preferred embodiment, the novel compositions are cosmetic compositions for the care and protection of skin, nail care compositions and formulations for decorative cosmetics.

Suitable cosmetic skin compositions are, for example, face lotions, face masks, deodorants and other cosmetic lotions. Compositions for use in decorative cosmetics comprise, for example, masking sticks, theater paints, mascara and eye shadows, lipsticks, kajal pencils, eye liners, rouges, powders and eyebrow pencils.

In addition, the ampholytic copolymers and polyelectrolyte complexes can be used in nose strips for pore cleansing, in anti-acne compositions, repellents, shaving compositions, depilatory compositions, feminine hygiene compositions and foot care compositions and in baby care.

The novel skin care compositions are in particular W/O or O/W skin creams, day and night creams, eye creams, face creams, anti-wrinkle creams, moisturizer creams, bleaching creams, vitamin creams, skin lotions, care lotions and moisturizer lotions.

Cosmetic skin and dermatological compositions based on the ampholytic copolymers and polyelectrolyte complexes described above have advantageous effects. The polymers can contribute, inter alia, to the moisturizing and conditioning of skin and to the improvement of the skin sensation. The polymers can also act as thickeners in the formulations. By adding the novel polymers, considerable improvement in skin tolerance can be achieved in certain formulations.

Cosmetic skin and dermatological compositions preferably comprise at least one ampholytic copolymer and/or one polyelectrolyte complex in an amount of from about 0.001 to 30, preferably from 0.01 to 20, very particularly preferably from 0.1 to 12% by weight, based on the total weight of the composition.

In particular light stabilizers based on ampholytic copolymers and polyelectrolyte complexes have the property of increasing the residence time of the UV-absorbing ingredients in comparison with conventional excipients, such as polyvinylpyrrolidone.

Depending on the field of use, the novel compositions can be applied in a form suitable for skin care, for example as cream, foam, gel, stick, mousse, milk, spray (pump spray or propellant-containing spray) or lotion.

In addition to the ampholytic copolymers and polyelectrolyte complexes, and suitable carriers, the cosmetic skin formulations may also comprise further active substances and excipients customary in skin cosmetics, as described above. These preferably include emulsifiers, preservatives, perfume oils, cosmetic active substances, such as phytantriol, vitamins A, E and C, retinol, bisabolol, panthenol, light stabilizers, bleaches, colorants, tinting compositions, tanning compositions, collagen, protein hydrolysis products, stabilizers, pH regulators, dyes, salts, thickeners, gel formers, consistency agents, silicones, moisturizers, refatting agents and further conventional additives.

Preferred oil and fat components of the cosmetic skin and dermatological compositions are the abovementioned mineral and synthetic oils, e.g. paraffins, silicone oils and aliphatic hydrocarbons of more than 8 carbon atoms, animal and vegetable oils, e.g. sunflower oil, coconut oil, avocado oil, olive oil or lanolin, or waxes, fatty acids, fatty esters, e.g. triglycerides of $C_6$-$C_{30}$-fatty acids, wax esters, e.g. jojoba oil, fatty alcohols, vaseline, hydrogenated lanolin and acetylated lanolin and mixtures thereof.

The novel ampholytic copolymers and polyelectrolyte complexes can also be mixed with conventional polymers if special properties are to be established.

For establishing specific properties, for example improvement of the sensation to touch, of the spreading behavior, of the water resistance and/or of the binding of active substances and excipients, such as pigments, the cosmetic skin and dermatological formulations may additionally comprise conditioning substances based on silicone compounds. Suitable silicone compounds are, for example, polyalkylsiloxanes, polyarylsiloxanes, polyarylalkylsiloxanes, polyethersiloxanes or silicone resins.

The preparation of the cosmetic or dermatological formulations can be effected by conventional processes known to a person skilled in the art.

Preferably, the cosmetic and dermatological compositions are in the form of emulsions, in particular in the form of water-in-oil (W/O) or oil-in-water (O/W) emulsions. However, it is also possible to choose other types of formulation, for example hydrodispersions, gels, oils, oleogels, multiple emulsions, for example in the form of W/O/W or O/W/O emulsions, anhydrous ointments or ointment bases, etc.

The preparation of emulsions is effected by known methods. In addition to at least one ampholytic copolymer and/or polyelectrolyte complex, the emulsions generally comprise conventional components, such as fatty alcohols, fatty esters and in particular fatty acid triglycerides, fatty acids, lanolin and derivatives thereof, natural or synthetic oils or waxes and emulsifiers in the presence of water. The choice of the additives specific to the emulsion type and the preparation of suitable emulsions are described, for example, in Schrader, Grundlagen und Rezepturen der Kosmetika, Hüthig Buch Verlag, Heidelberg, 2nd Edition, 1989, third part, which is hereby incorporated by reference.

A suitable emulsion, for example for a skin cream, etc., generally comprises an aqueous phase, which is emulsified in an oil or fat phase by means of a suitable emulsifier system. For providing the aqueous phase, a novel ampholytic copolymer and/or a polyelectrolyte complex may be used.

Preferred fat components which may be present in the fat phase of the emulsions are: hydrocarbon oils, such as liquid paraffin, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils which begin to distill under atmospheric pressure at about 250° C. and the end point of whose distillation is 410° C., e.g. vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fat phase may also comprise silicone oils soluble in other oils, such as dimethylpolysiloxane, methylphenylpolysiloxane and the silicone-glycol copolymer, fatty acids and fatty alcohols.

In addition to the ampholytic copolymers and polyelectrolyte complexes, it is also possible to use waxes, e.g. carnauba wax, candililla wax, beeswax, microcrystalline wax, ozokerite wax and calcium, magnesium and aluminum oleates, myristates, linoleates and stearates.

Furthermore, a novel emulsion may be present as an O/W emulsion. Such an emulsion usually comprises an oil phase, emulsifiers which stabilize the oil phase in the aqueous phase, and an aqueous phase, which is usually present in thickened form. Preferred emulsifiers are O/W emulsifiers, such as polyglyceryl esters, sorbitan esters or partly esterified glycerides.

According to a further preferred embodiment, the novel compositions are a shower gel, a shampoo formulation or a bath preparation.

Such formulations comprise at least one ampholytic copolymer and/or one polyelectrolyte complex and usually anionic surfactants as base surfactants and amphoteric and/or nonionic surfactants as cosurfactants. Further suitable active substances and/or excipients are generally selected from lipids, perfume oils, dyes, organic acids, preservatives and antioxidants and thickeners/gel formers, skin conditioners and moisturizers.

These formulations preferably comprise from 2 to 50, preferably from 5 to 40, particularly preferably from 8 to 30% by weight, based on the total weight of the formulation, of surfactants.

All anionic, neutral, amphoteric or cationic surfactants usually used in body cleansing compositions may be used in the wash, shower and bath preparations.

Suitable anionic surfactants are, for example, alkyl sulfates, alkyl ether sulfates, alkyl sulfonates, alkylaryl sulfonates, alkyl succinates, alkyl sulfosuccinates, N-alkoylsarcosinates, acyltaurates, acylisethionates, alkyl phosphates, alkyl ether phosphates, alkyl ether carboxylates, alpha-olefinsulfonates, in particular the alkali metal and alkaline earth metal salts, for example sodium, potassium, magnesium and calcium salts, and ammonium and triethanolamine salts. The alkyl ether sulfates, alkyl ether phosphates and alkyl ether carboxylates may have from 1 to 10 ethylene oxide or propylene oxide units, preferably from 1 to 3 ethylene oxide units, in the molecule.

These include, for example, sodium laurylsulfate, ammonium laurylsulfate, sodium lauryl ether sulfate, ammonium lauryl ether sulfate, sodium laurylsarcosinate, sodium oleylsuccinate, ammonium laurylsulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, or alkyl amphodiacetates and -dipropionates.

For example, cocodimethylsulfopropylbetaine, laurylbetaine, cocoamidopropylbetaine or sodium cocamphopropionate may be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is from about 6 to 60 moles per mole of alcohol. Furthermore, alkylamine oxides, mono- or dialkylalkanolamides, fatty esters of polyethylene glycols, ethoxylated fatty amides, alkylpolyglycosides or sorbitan ether esters are suitable.

In addition, the wash, shower and bath preparations may comprise conventional cationic surfactants, such as quaternary ammonium compounds, for example cetyltrimethylammonium chloride.

Furthermore, the shower gel/shampoo formulations may comprise thickeners, such as sodium chloride, PEG-55, propylene glycol oleate, PEG-120 methylglucose dioleate and others, and preservatives, further active substances and excipients and water.

According to a particularly preferred embodiment, the novel composition is a hair treatment composition.

Novel hair treatment compositions preferably comprise at least one ampholytic copolymer and/or one polyelectrolyte complex in an amount of from about 0.1 to 30, preferably from 0.5 to 20% by weight, based on the total weight of the composition.

The novel hair treatment compositions are preferably in the form of a foam setting composition, hair mousse, hair gel, shampoo, hairspray, hair foam, damaged end fluid, neutralizing composition for permanent waves, hair color and bleach or hot-oil treatment. Depending on the field of use, the cosmetic hair formulations can be applied in the form of an (aerosol) spray, (aerosol) foam, gel, gel spray, cream, lotion or wax. Hairsprays comprise both aerosol sprays and pump sprays without propellant. Hair foams comprise both aerosol foams and pump foams without propellant. Hairsprays and hair foams preferably comprise predominantly or exclusively water-soluble or water-dispersible components. If the compounds used in the novel hairsprays and hair foams are water-dispersible, they may be used in the form of aqueous microdispersions having particle diameters of, usually, from 1 to 350 nm, preferably from 1 to 250 nm. The solids contents of these preparations are usually from about 0.5 to 20% by weight. As a rule, these microdispersions require no emulsifiers or surfactants for their stabilization.

In a preferred embodiment, the novel cosmetic hair formulations comprise
  a) from 0.05 to 20% by weight of at least one ampholytic copolymer and/or polyelectrolyte complex, as defined above,
  b) from 20 to 99.95% by weight of water and/or alcohol,
  c) from 0 to 50% by weight of at least one propellant,
  d) from 0 to 5% by weight of at least one emulsifier,
  e) from 0 to 3% by weight of at least one thickener and
  f) up to 25% by weight of further components, Alcohol is to be understood as meaning all alcohols customary in cosmetics, e.g. ethanol, isopropanol and n-propanol.

Further components are to be understood as meaning the additives customary in cosmetics, for example propellants, antifoams, surface-active compounds, i.e. surfactants, emulsifiers, foam formers and solubilizers. The surface-active compounds used may be anionic, cationic, amphoteric or neutral. Further conventional components may furthermore be, for example, preservatives, perfume oils, opacifiers, active substances, UV filters, care substances, such as panthenol, collagen, vitamins, protein hydrolysis products, alpha- and beta-hydroxycarboxylic acids, stabilizers, pH regulators, dyes, viscosity regulators, gel formers, salts, moisturizers, refatting agents, complexing agents and further conventional additives.

These furthermore include all styling and conditioner polymers known in cosmetics, which may be used in combination with the novel polymers if very special properties are to be established.

For establishing specific properties, the formulations may additionally comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds, such as amodimethicone (CTFA).

The novel ampholytic copolymers and polyelectrolyte complexes are particularly suitable as setting compositions in hairstyling formulations, in particular hairsprays (aerosol sprays and pump sprays without propellant) and hair foams (aerosol foams and pump foams without propellant).

In a preferred embodiment, spray formulations comprise
a) from 0.1 to 10% by weight of at least one ampholytic copolymer and/or polyelectrolyte complex, as defined above,
b) from 20 to 99.9% by weight of water and/or alcohol,
c) from 0 to 70% by weight of at least one propellant,
d) from 0 to 20% by weight of further components.

Propellants are the propellants usually used for hairsprays or aerosol foams. Mixtures of propane/butane, pentane, dimethyl ether, 1,1-difluoroethane (HFC-152 a), carbon dioxide, nitrogen or compressed air are preferred.

A formulation for aerosol hair foams which is preferred according to the invention comprises
a) from 0.1 to 10% by weight of at least one ampholytic copolymer and/or polyelectrolyte complex, as defined above,
b) from 55 to 99.8% by weight of water and/or alcohol,
c) from 5 to 20% by weight of a propellant,
d) from 0.1 to 5% by weight of an emulsifier,
e) from 0 to 10% by weight of further components.

Emulsifiers which may be used are all emulsifiers usually used in hair foams. Suitable emulsifiers may be nonionic, cationic or anionic or amphoteric.

Examples of nonionic emulsifiers (INCI nomenclature) are laureths, e.g. laureth-4; ceteths, e.g. cetheth-1, polyethylene glycol cetyl ether, cetearyths, e.g. cetheareth-25, polyglycol fatty acid glycerides, hydroxylated lecithin, lactyl esters of fatty acids, alkylpolyglycosides.

Examples of cationic emulsifiers are cetyldimethyl-2-hydroxyethylammonium dihydrogen phosphate, cetyltrimonium chloride, cetyltrimonium bromide, cocotrimonium methylsulfate, Quaternium-1 to x (INCI).

Anionic emulsifiers can be selected, for example, from the group consisting of the alkyl sulfates, alkyl ether sulfate, alkyl sulfonates, alkylaryl sulfonates, alkyl succinates, alkyl sulfosuccinates, N-alkoylsarcosinates, acryl taurates, acryl isethionates, alkyl phosphates, alkyl ether phosphates, alkyl ether carboxylates, alpha-olefinsulfonates, in particular the alkali metal and alkaline earth metal salts, e.g. sodium, potassium, magnesium or calcium salts, and ammonium and triethanolamine salts. The alkyl ether sulfates, alkyl ether phosphates and alkyl ether carboxylates may have from 1 to 10 ethylene oxide or propylene oxide units, preferably from 1 to 3 ethylene oxide units, in the molecule.

A formulation suitable according to the invention for styling gels may be composed, for example, of:
a) from 0.1 to 10% by weight of at least one ampholytic copolymer and/or polyelectrolyte complex, as defined above,
b) from 80 to 99.85% by weight of water and/or alcohol,
c) from 0 to 3, preferably from 0.05 to 2% by weight of a gel former,
d) from 0 to 20% by weight of further components.

In general, the novel polyelectrolyte complexes already have a self-thickening effect so that in many cases it is possible to dispense with the use of gel formers in the preparation of gels. However, their use may be advantageous for establishing specific rheological properties or other performance characteristics of the gels. Gel formers which may be used are all gel formers customary in cosmetics. These include slightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) Paraffinum Liquidum (INCI), sodium acrylate copolymers (and) Paraffinum Liquidum (and) PPG-1 trideceth-6, acrylamidopropyltrimonium chloride/acrylamide copolymers, steareth-10 allyl ether acrylate copolymers, polyquaternium-37 (and) Paraffinum Liquidum (and) PPG-1 trideceth-6, polyquaternium 37 (and) propylene glycol dicaprate dicaprylate (and) PPG-1 trideceth-6, polyquaternium-7, polyquaternium-44.

The novel ampholytic copolymers and/or polyelectrolyte complexes may be used as conditioners in cosmetic formulations.

The novel ampholytic copolymers and/or polyelectrolyte complexes, as defined above, can preferably be used as setting compositions and/or conditioners in shampoo formulations. Preferred shampoo formulations comprise
a) from 0.05 to 10% by weight of at least one ampholytic copolymer and/or polyelectrolyte complex, as defined above,
b) from 25 to 94.95% by weight of water,
c) from 5 to 50% by weight of surfactants,
d) from 0 to 5% by weight of a further conditioner
e) from 0 to 10% by weight of further cosmetic components.

In the shampoo formulations, it is possible to use all anionic, neutral, amphoteric or cationic surfactants usually used in shampoos.

Suitable anionic surfactants are, for example, alkyl sulfates, alkyl ether sulfates, alkyl sulfonates, alkylaryl sulfonates, alkylsuccinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium and calcium salts, and ammonium and triethanolamine salts. The alkyl ether sulfates, alkyl ether phosphates and alkyl ether carboxylates may have from 1 to 10 ethylene oxide or propylene oxide units, preferably from 1 to 3 ethylene oxide units, in the molecule.

For example, sodium laurylsulfate, ammonium laurylsulfate, sodium lauryl ethyl sulfate, ammonium lauryl ether sulfate, sodium lauroylsarcosinate, sodium oleylsuccinate, ammonium laurylsulfosuccinate, sodium dodecylbenzenesulfonate and triethanolamine dodecylbenzenesulfonate are suitable.

Suitable amphoteric surfactants are, for example, alkylbetaines, alkylamidopropylbetaines, alkylsulfobetaines, alkyl glycinates, alkyl carboxylglycinates, alkyl amphoacetates or -propionates or alkyl amphodiacetates or -dipropionates.

For example, cocodimethylsulfopropylbetaine, laurylbetaine, cocamidopropylbetaine or sodium cocamphopropionate may be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is from about 6 to 60 moles per mole of alcohol. Furthermore, alkylamine oxides, mono- or dialkylalkanolamides, fatty esters of polyethylene glycols, alkylpolyglycosides or sorbitan ether esters are suitable.

In addition, the shampoo formulations may comprise conventional cationic surfactants, e.g. quaternary ammonium compounds, for example cetyltrimethylammonium chloride.

Conventional conditioners in combination with the ampholytic copolymers and/or polyelectrolyte complexes may be used in the shampoo formulations for achieving specific effects. These include, for example, the abovementioned cationic polymers having the name Polyquaternium according to INCI, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamide copolymers (polyquaternium-7). It is furthermore possible to use protein hydrolysis products, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and amino-functional silicone compounds, such as amodimethicone (CTFA). Furthermore, cationic guar derivatives, such as guar hydroxypropyltrimonium chloride (INCI), may be used.

The invention furthermore relates to the use of an ampholytic copolymer and/or polyelectrolyte complex as an excipient in pharmacy, preferably as or in coating material(s) for solid dosage forms, for modifying rheological properties, as a surface-active compound, as or in adhesive(s) and as or in coating material(s) for the textile, paper, printing and leather industry.

The nonlimiting examples which follow illustrate the invention.

EXAMPLES

General Preparation Method (A): Solution Polymerization in Ethanol/Water

Example 15

600 g of a 30% strength polymer solution (TBA/TBMA/AS/DMAPMAM=65:10:22:3)

| Feed 1: | Monomer mixture comprising: |
| --- | --- |
| 117 g | of tert-butyl acrylate |
| 18 g | of tert-butyl methacrylate |

| -continued | |
| --- | --- |
| 39.6 g | of acrylic acid |
| 5.4 g | of dimethylaminopropylmethacrylamide |
| 147 g | of ethanol |
| Feed 2: | Initiator solution comprising: |
| 0.72 g | of Wako ® 50 [2,2'-azobis(2-amidinopropane) dihydrochloride] |
| 42 g | of water |
| Feed 3: | Initiator solution comprising: |
| 0.9 g | of 75% strength tert-butyl perpivalate |
| 31.5 g | of ethanol |
| Feed 4: | Initiator solution comprising: |
| 0.9 g | of 75% strength tert-butyl perpivalate |
| 31.5 g | of ethanol |
| Feed 5: | |
| 41.6 g | of 2-amino-2-methyl-propanol (AMP) |
| 28 g | of water |
| 70 g | of ethanol |

16.35 g of feed 1, 2.15 g of feed 2, 77 g of water and 90 g of ethanol were initially taken in a stirred apparatus having a reflux condenser, internal thermometer and four separate feed apparatuses, and the mixture was heated to about 70° C. with stirring. After the prepolymerization, detectable by a slight increase in the viscosity, the remainder of feed 1 was added at 70° C. in the course of three hours and the remainder of feed 2 in the course of four hours, the internal temperature being increased to about 73° C. The reaction solution was stirred for about a further two hours at 70° C. and then feed 3 was metered in in the course of 30 minutes at 70° C. After the addition, stirring was continued for about a further two hours at 80° C. Thereafter, feed 4 was metered in in the course of 10 minutes and polymerization was continued for about another two hours at 80° C. The polymer solution was neutralized with AMP (feed 5, duration of addition 10 minutes). An aqueous/ethanolic solution of about 30% strength was obtained.

The polymers No. 1-26 and 35 to 39 were prepared analogously.

General Preparation Method (B):

Solution polymerization in ethanol/water with subsequent steam distillation

Example 29

900 g of a polymer solution of about 20% strength (TBA/VP/AS/MAS/VI=40:40:10:5:5)

| Feed 1: | Monomer mixture comprising: |
| --- | --- |
| 72 g | of tert-butyl acrylate |
| 72 g | of vinylpyrrolidone |
| 18 g | of acrylic acid |
| 9 g | of methacrylic acid |
| 9 g | of vinylimidazole |
| 15 g | of N,N-dimethylethanolamine |

-continued

| Feed 2: | Initiator solution comprising: |
|---|---|
| 0.18 g | of Wako 50 ® [2,2'-azobis(2-amidinopropane) dihydrochloride] |
| 50 g | of water |
| Feed 3: | Initiator solution comprising: |
| 0.9 g | of 75% strength tert-butyl perpivalate |
| 63 g | of ethanol |
| Feed 4: | |
| 360 g | of ethanol |

9 g of feed 1, 2.5 g of feed 2, 75 g of water and 75 g of ethanol were initially taken in a stirred apparatus having a reflux condenser, internal thermometer and four separate feed apparatuses, and the mixture was heated to about 63° C. with stirring. After the prepolymerization, detectable by a slight increase in viscosity, the remainder of feed 1 was added at 65° C. in the course of three hours and the remainder of feed 2 in the course of four hours. The reaction solution was stirred for about a further two hours at 65° C. Feed 3 was metered in at about 75° C. in 30 minutes, and the polymer mixture was stirred for about a further two hours at 80° C. Ethanol was then removed from the reaction solution by steam distillation at an external temperature of 120° C. The polymer solution was cooled to about 40° C. and diluted with ethanol (feed 4). The polymer solution was brought to pH 8-8.3 with N,N-dimethylethanolamine and to a solids content of 20% with water. A clear pale yellow solution was obtained.

The polymers No. 27-34 and 40 to 42 were prepared analogously.

TABLE 1

| Ex. No. | TBA | OAA | TMBA | NtBAM | VP | AA | MAA | NtBAEMA | VI | DMAP-MAM | Amine/Ng. | K value |
|---|---|---|---|---|---|---|---|---|---|---|---|---|
| 1 | 80 | — | — | — | — | 18 | — | — | 2 | — | AMP/90 | 41.8 |
| 2 | 80 | — | — | — | — | 17 | — | 3 | — | — | AMP/90 | 42.7 |
| 3 | 75 | — | — | — | — | 22 | — | 3 | — | — | AMP/85 | 38.2 |
| 4 | 75 | — | — | — | — | 20 | — | — | 5 | — | AMP/85 | 39.4 |
| 5 | 75 | — | — | — | — | 15 | 5 | 5 | — | — | AMP/85 | 43.4 |
| 6 | 70 | — | — | — | — | 17 | 10 | 3 | — | — | AMP/85 | 47.8 |
| 7 | 70 | — | — | — | — | 17 | 10 | — | — | 3 | AMP/85 | 45.7 |
| 8 | 70 | — | — | — | — | 15 | 10 | — | 5 | — | AMP/85 | 46.9 |
| 9 | 70 | — | — | — | — | 14 | 12 | — | 4 | — | AMP/85 | 48.1 |
| 10 | 70 | 5 | — | — | — | 22 | — | 3 | — | — | TEA/90 | 46.8 |
| 11 | 70 | 5 | — | — | — | 22 | — | — | 3 | — | TEA/90 | 45.1 |
| 12 | 70 | 5 | — | — | — | 22 | — | — | — | 3 | TEA/90 | 47.3 |
| 13 | 65 | — | 10 | — | — | 22 | — | 3 | — | — | AMP/90 | 45.3 |
| 14 | 65 | — | 10 | — | — | 22 | — | — | 3 | — | AMP/90 | 44.6 |
| 15 | 65 | — | 10 | — | — | 22 | — | — | — | 3 | AMP/90 | 46.6 |
| 16 | 60 | — | 10 | — | — | 15 | 10 | — | 5 | — | AMP/90 | 51.0 |
| 17 | 67 | — | — | 10 | — | 20 | — | 3 | — | — | AMP/85 | 44.7 |
| 18 | 67 | — | — | 10 | — | 20 | — | — | 3 | — | AMP/85 | 44.1 |
| 19 | 67 | — | — | 10 | — | 20 | — | — | — | 3 | AMP/85 | 43.8 |
| 20 | 60 | — | — | 12 | — | 24 | — | 4 | — | — | AMP/85 | 46.4 |
| 21 | 60 | — | — | 12 | — | 24 | — | — | 4 | — | AMP/85 | 47.7 |
| 22 | 60 | — | — | 12 | — | 24 | — | — | — | 4 | AMP/85 | 49.2 |
| 23 | 60 | — | — | 15 | — | 20 | — | 5 | — | — | AMP/85 | 43.6 |
| 24 | 60 | — | — | 15 | — | 20 | — | — | 5 | — | AMP/85 | 45.2 |
| 25 | 60 | — | — | 15 | — | 20 | — | — | — | 5 | AMP/85 | 44.7 |
| 26 | 55 | — | — | 20 | — | 22 | — | — | — | 3 | AMP/85 | 49.6 |
| 27 | 48 | — | — | — | 32 | 17 | — | — | 3 | — | DMEA to pH 8.0 | 39.5 |
| 28 | 45 | — | — | — | 30 | 10 | 10 | — | — | 5 | DMEA to pH 8.0 | 52.9 |
| 29 | 40 | — | — | — | 40 | 10 | 5 | — | 5 | — | DMEA to pH 8.0 | 47.0 |
| 30 | 40 | — | — | — | 40 | 17 | — | 3 | — | — | DMEA to pH 8.0 | 39.6 |
| 31 | 40 | — | — | — | 40 | 17 | — | — | 3 | — | DMEA to pH 8.0 | 45.9 |
| 32 | 35 | — | — | — | 45 | 20 | — | 5 | — | — | DMEA to pH 8.0 | 45.3 |
| 33 | 35 | — | — | — | 45 | 20 | — | — | 5 | — | DMEA to pH 8.0 | 43.8 |
| 34 | 30 | — | — | 20 | 30 | 10 | — | 10 | — | — | DMEA to pH 8.0 | 42.5 |

TABLE 2

| Ex. No. | TBA | EMA | VP | AA | MAA | VI | NtBAEMA |
|---|---|---|---|---|---|---|---|
| 35 | 68 | — | — | 3 | 22 | 7 | — |
| 36 | 65 | — | — | 5 | 20 | — | 10 |
| 37 | 44 | 30 | — | 3 | 20 | 3 | — |
| 38 | 40 | 30 | — | 3 | 20 | 7 | — |
| 39 | 40 | 30 | — | 5 | 20 | — | 5 |
| 40 | 50 | — | 30 | — | 15 | 5 | — |
| 41 | 50 | — | 25 | 3 | 15 | 7 | — |
| 42 | 45 | — | 30 | — | 15 | — | 10 |

| | |
|---|---|
| TBA | tert-butyl acrylate |
| EMA | ethyl methacrylate |
| OAA | N-tert-octylacrylamide |
| TBMA | tert-butyl methacrylate |
| NtBAM | N-tert-butylacrylamide |
| VP | vinylpyrrolidone |
| AA | acrylic acid |
| MAA | methacrylic acid |
| NtBAEMA | N-(tert-butyl) aminoethyl methacrylate |
| VI | vinylimidazole |
| DMAPMAM | dimethylaminopropylmethacrylamide |
| Amine | AMP = 2-amino-2-methylpropanol |
| | TEA = triethanolamine |
| | DMEA = dimethylethanolamine |
| Ng. | Degree of neutralization |
| K value | 1% strength in N-methylpyrrolidone |

Use Examples:

I) Use in Hair Cosmetics:

1) VOC 80 aerosol hairspray (examples No. 1-26)

| | |
|---|---|
| Polymer 1–26 (30% strength aqueous ethanolic solution) | 10.0 |
| Water | 15.0 |
| Dimethyl ether | 40.0 |
| Ethanol | 35.0 |

Further Additives:

Preservative, soluble ethoxylated silicone, perfume, antifoam . . . .

2) VOC 80 aerosol hairspray (examples No. 27-34)

| | |
|---|---|
| Polymer 27, 28, 29, 30, 31, 32, 33, 34 (20% strength aqueous ethanolic solution) | 15.0 |
| Water | 11.0 |
| Dimethyl ether | 40.0 |
| Ethanol | 34.0 |

Further Additives:

Preservative, soluble ethoxylated silicone, perfume, antifoam . . . .

3) VOC 55 aerosol hairspray (examples No. -35-65)

| | |
|---|---|
| Polymer 1–26, 35, 36, 37, 38, 39 (30% strength aqueous ethanolic solution) | 6.67 |
| Water | 41.7 |
| Dimethyl ether | 40.0 |
| Ethanol | 11.7 |

Further Additives:

Preservative, soluble ethoxylated silicone, perfume, antifoam . . . .

4) VOC 55 aerosol hairspray (examples No. -66-76)

| | |
|---|---|
| Polymer 27, 28, 29, 30, 31, 32, 33, 34, 40, 41, 42 (20% strength aqueous ethanolic solution) | 10.0 |
| Water | 39.0 |
| Dimethyl ether | 40.0 |
| Ethanol | 11.0 |

Further Additives:

Preservative, soluble ethoxylated silicone, perfume, antifoam . . . .

5) VOC 55 aerosol hairspray (examples No. -77-107)

| | |
|---|---|
| Polymer 1–26, 35, 36, 37, 38, 39 (30% strength aqueous ethanolic solution | 6.7 |
| Luvimer ® Low VOC (neutralized with AMP) | 1.0 |
| Water | 40.6 |
| Dimethyl ether | 40.0 |
| Ethanol | 11.7 |

Further Additives:

Preservative, soluble ethoxylated silicone, perfume, antifoam . . . .

6) VOC 55 aerosol hairspray (examples No. -108-118)

| | |
|---|---|
| Polymer 27, 28, 29, 30, 31, 32, 33, 34, 40, 41, 42 (20% strength aqueous ethanolic solution) | 10.0 |
| Luviset PUR (30% strength solution) | 5.0 |
| Water | 34.5 |
| Dimethyl ether | 40.0 |
| Ethanol | 10.5 |

Further Additives:

Preservative, soluble ethoxylated silicone, perfume, antifoam . . . .

7) VOC 55 pump spray (examples No. -119-149)

| | |
|---|---|
| Polymer 1–26, 35, 36, 37, 38, 39 (30% strength aqueous ethanolic solution) | 6.67 |
| Water | 41.7 |
| Ethanol | 51.7 |

Further Additives:

Preservative, soluble ethoxylated silicone, perfume, antifoam . . . .

8) VOC 55 pump spray (examples No. -150-160)

| | |
|---|---|
| Polymer 27, 28, 29, 30, 31, 32, 33, 34, 40, 41, 42 (20% strength aqueous ethanolic solution) | 10.0 |
| Luviset ® PUR (30% strength solution) | 5.0 |
| Water | 34.5 |
| Ethanol | 50.5 |

Further Additives:

Preservative, soluble ethoxylated silicone, perfume, antifoam . . . .

9) Foam setting composition (examples No. -161-176)

| | |
|---|---|
| Polymer No. 3, 4, 5, 6, 7, 8, 9, 13, 20, 21, 22, 35, 36, 37, 38, 39 (30% strength solution) | 5.0 |
| Luviflex ® Soft (10% strength aqueous solution, pH=7) | 15.0 (acrylate copolymer, from BASF) |
| Cremophor ® A 25 | 0.2 (ceteareth 25, from BASF) |
| Comperlan ® KD | 0.1 (coamide DEA, from Henkel) |
| Water | 69.7 |
| Dimethyl ether | 10.0 |

Further additives: perfume, preservative . . . .

Preparation: Weigh in and dissolve with stirring. Fill and add propellant.

10) Foam setting composition (examples No. 177-183)

| | |
|---|---|
| Polymer No. 28, 32, 33, 34, 40, 41, 42 (20% strength solution) | 15.0 |
| Cremophor ® A 25 | 0.2 (ceteareth 25, from BASF) |
| Comperlan ® KD | 0.1 (coamide DEA, from Henkel) |
| Water | 74.7 |
| Dimethyl ether | 10.0 |

Further additives: perfume, preservative . . . .

Preparation: Weigh in and dissolve with stirring. Fill and add propellant.

11) Hair gels (examples No. -184-225)

| | [%] |
|---|---|
| Phase 1: | |
| Polymer 1-26, 35, 36, 37, 38, 39 (30% strength solution) or polymer 27, 28, 29, 30, 31, 32, 33, 34, 40, 41, 42 (20% strength solution) | 10.0 |
| Distilled water | 15.0 to 49.0 |
| Aminomethylpropanol (38% strength solution) | 1.0 |
| Further additives: | |
| Preservative, soluble ethoxylated silicone, perfume . . . | |
| Phase 2: | |
| Acrylic acid/beheneth-25 methacrylate copolymers (Aculyn ® 28 from Rohm und Haas, 1% strength aqueous suspension) | 50.0 |

Preparation: The components of phases 1 and 2 are weighed in separately and homogenized. Phase 2 is slowly stirred into phase 1. A clear, solid gel forms.

II) Use in Hair Cosmetics:

12) Standard O/W cream (examples No. -226-237)

| Oil Phase: | % | CTFA name |
|---|---|---|
| Cremophor A6 | 3.5 | Ceteareth-6 (and) Stearyl Alkohol |
| Cremophor A25 | 3.5 | Ceteareth-25 |
| Glyceryl monostearate s.e | 2.5 | Glyceryl Stearate |
| Liquid paraffin | 7.5 | Paraffin Oil |
| Cetyl alcohol | 2.5 | Cetyl Alkohol |
| Luvitol EHO | 3.2 | Cetearyl Octanoate |
| Vitamin E acetate | 1.0 | Tocopheryl Acetate |
| Nip-Nip | 0.1 | Methyl and Propyl 4-hydroxybenzoate (7:3) |

| Aqueous phase: | % | CTFA name |
|---|---|---|
| Polymer No. 12, 27, 28, 29, 30, 31, 32, 33, 34, 40, 41, 42 (20% strength aqueous solution) | 3.0 | |
| Water | 74.6 | |
| 1,2-Propylene glycol | 1.5 | Propylene Glycol |
| Germall II | 0.1 | Imidazolidinyl-Urea |

Preparation: The components are weighed in and the oil phase and aqueous phase are homogenized separately at about 80° C. with stirring. The aqueous phase is slowly stirred into the oil phase and the mixture is cooled to room temperature with stirring.

13) Day lotion (examples No. -238-249)

| Oil phase: | % | CTFA name |
|---|---|---|
| Cremophor A6 | 1.5 | Ceteareth-6 (and) Stearyl Alkohol |
| Cremophor A25 | 1.5 | Ceteareth-25 |
| Glyceryl monostearate s.e. | 5.0 | Glyceryl Stearate |
| Uvinul MS 40 | 0.5 | Bezophenone-4 |
| Liquid paraffin | 3.5 | Paraffin Oil |
| Cetyl alcohol | 0.5 | Cetyl Alkohol |
| Luvitol EHO | 10.0 | Cetearyl Octanoate |
| D-Panthenol 50 P | 3.0 | Panthenol and propylene glycol |
| Vitamin E acetate | 1.0 | Tocopheryl Acetate |
| Tegiloxan 100 | 0.3 | Dimethicone |
| Nip-Nip | 0.1 | Methyl and Propyl 4-hydroxybenzoate (7:3) |

| Aqueous phase: | % | |
|---|---|---|
| Polymer No. 12, 27, 28, 29, 30, 31, 32, 33, 34, 40, 41, 42 (20% strength aqueous solution) | 1.5 | |
| Water | 70.0 | |
| 1,2-Propylene glycol | 1.5 | Propylene Glycol |
| Germall II | 0.1 | Imidazolidinyl-Urea |

Preparation: The components are weighed in and the oil phase and aqueous phase are homogenized separately at about 80° C. with stirring. The aqueous phase is slowly stirred into the oil phase and the mixture is cooled to room temperature with stirring.

We claim:

1. An ampholytic copolymer comprising a molar excess of anionogenic and/or anionic groups, obtained by free radical polymerization of
   a) at least one branched $C_3$-$C_5$-alkyl acrylate,
   b) acrylic acid and methacrylic acid, with the proviso that the proportion by weight of acrylic acid is equal to or greater than the proportion by weight of methacrylic acid, and
   c) a monomer composition comprising
      c1) at least one compound having an $\alpha,\beta$-ethylenically unsaturated double bond capable of free radical polymerization and at least one anionogenic and/or anionic group per molecule and
      c2) at least one compound having an $\alpha,\beta$-ethylenically unsaturated double bond capable of free radical polymerization and at least one cationogenic and/or cationic group per molecule,
   the molar ratio of anionogenic and anionic groups of component c1) to cationogenic and cationic groups of component c2) being about 1:1.

2. The copolymer according to claim 1, the component a) comprising tert-butyl acrylate.

3. The copolymer according to claim 1, wherein component c1) is selected from the group consisting of $\alpha,\beta$-ethylenically unsaturated mono- and dicarboxylic acids, sulfonic acids, phosphonic acids and mixtures thereof.

4. The copolymer according to claim 1, wherein component c1) is selected from the group consisting of acrylic acid, methacrylic acid, itaconic acid and mixtures thereof.

5. The copolymer according to claim 1, wherein component c2) is selected from the group consisting of esters of $\alpha,\beta$-ethylenically unsaturated mono- and dicarboxylic acids with amino alcohols which may be mono- or dialkylated at the amine nitrogen, amides of $\alpha,\beta$-ethylenically unsaturated mono- and dicarboxylic acids with diamines which have at least one primary and secondary amino group, N,N-diallylamine, N,N-diallyl-N-alkylamines and the derivatives thereof, vinyl- and allyl-substituted nitrogen heterocycles, vinyl- and allyl-substituted heteroaromatic compounds and mixtures thereof.

6. The copolymer according to claim 1, wherein component c2) is selected from the group consisting of N-vinylimidazole, N-(tert-butylamino)ethyl (meth)acrylate, N,N-dimethylaminoethyl (meth)acrylate, N-[3-(dimethylamino)propyl]-(meth)acrylamide and mixtures thereof.

7. The copolymer according to claim 1, which consists of repeating units of
   tert-butyl acrylate,
   acrylic acid and methacrylic acid, and
   N-(tert-butyl)aminoethyl (meth)acrylate or N-[3-(dimethylamino)propyl]-methacrylamide or N,N-dimethylaminoethyl methacrylate or N-vinylimidazole.

8. The copolymer according to claim 1, which consists of repeating units of
   tert-butyl acrylate,
   tert-butyl methacrylate,
   acrylic acid and methacrylic acid, and
   N-(tert-butyl)aminoethyl (meth)acrylate or N-[3-(dimethylamino)propyl]-methacrylamide or N,N-dimethylaminoethyl methacrylate or —N-vinylimidazole.

9. An ampholytic copolymer comprising a molar excess of anionogenic and/or anionic groups and being obtained by free radical polymerization, which consists of repeating units of
   tert-butyl acrylate,
   acrylic acid and methacrylic acid,
   N-(tert-butyl)acrylamide, and
   —N-(tert-butyl)aminoethyl (meth)acrylate or N-[3-(dimethylamino)propyl]-methacrylamide or N,N-dimethylaminoethyl methacrylate or N-vinylimidazole,
   the molar ratio of N-(tert-butyl)acrylamide) to N-(tert-butyl)aminoethyl (meth)acrylate or N-[3-(dimethylamino)propyl]-methacrylamide or N,N-dimethylaminoethyl methacrylate or N-vinylimidazole being about 1:1.

10. An ampholytic copolymer comprising a molar excess of anionogenic and/or anionic groups and being obtained by free radical polymerization, which consists of repeating units of
    tert-butyl acrylate,
    acrylic acid and/or methacrylic acid,
    vinylpyrrolidone and
    —N-(tert-butyl)aminoethyl (meth)acrylate or N-[3-(dimethylamino)propyl]-methacrylamide or N,N-dimethylaminoethyl methacrylate or N-vinylimidazole,
    the molar ratio of vinylpyrrolidone to N-(tert-butyl)aminoethyl (meth)acrylate or N-[3-(dimethylamino)propyl]-methacrylamide or N,N-dimethylaminoethyl methacrylate or N-vinylimidazole being about 1:1.

11. An ampholytic copolymer comprising a molar excess of anionogenic and/or anionic groups and being obtained by free radical polymerization, which consists of repeating units of
    tert-butyl acrylate,
    acrylic acid and/or methacrylic acid,
    N-(tert-butyl)acrylamide,
    vinylpyrrolidone and
    N-(tert-butyl)aminoethyl (meth)acrylate or N-[3-(dimethylamino)propyl]-methacrylamide or N,N-dimethylaminoethyl methacrylate or N-vinylimidazole,
    the molar ratio of vinylpyrrolidone to N-(tert-butyl)aminoethyl (meth)acrylate or N-[3-(dimethylamino)propyl]methacrylamide or N,N-dimethylaminoethyl methacrylate or N-vinylimidazole being about 1:1.

12. The copolymer according to claim 1, which comprises, incorporated in the form of polymerized units,
    a) tert-butyl acrylate,
    b) acrylic acid and methacrylic acid,
    c) N-(tert-butyl)aminoethyl acrylate or N-(tert-butyl)aminoethyl (meth)acrylate or N-[3-(dimethylamino)propyl]methacrylamide or N,N-dimethylaminoethyl methacrylate or N-vinylimidazole,
    d) optionally, vinylpyrrolidone and
    e) at least one compound which is selected from $C_1$-$C_3$-alkyl methacrylates, hydroxy-$C_1$-$C_3$-alkyl methacrylates and mixtures thereof,
    with the proviso that the proportion by weight of component a) is equal to or greater than the proportion by weight of component e).

13. The copolymer according to claim 1, which consists of repeating units of
    tert-butyl acrylate,
    acrylic acid and methacrylic acid,
    N-(tert-butyl)aminoethyl (meth)acrylate or N-vinylimidazole and
    ethyl methacrylate,
    with the proviso that the proportion by weight of tert-butyl acrylate is equal to or greater than the proportion by weight of ethyl methacrylate.

14. The copolymer according to claim 1, which consists of repeating units of
    tert-butyl acrylate,
    acrylic acid and methacrylic acid,
    N-vinylpyrrolidone, N-(tert-butyl)aminoethyl (meth)acrylate or N-vinylimidazole and ethyl methacrylate, with the proviso that the proportion by weight of tert-butyl acrylate is equal to or greater than the proportion by weight of ethyl methacrylate.

15. The copolymer according to claim 1, which comprises, based in each case on the total weight of the monomers used for the polymerization, from 20 to 80% by weight of tert-butyl acrylate and ethyl methacrylate, with the proviso that the proportion by weight of tert-butyl acrylate is equal to or greater than the proportion by weight of ethyl methacrylate, from 5 to 30% by weight of acrylic acid and methacrylic acid, from 1 to 20% by weight of a monomer composition comprising methacrylic acid and N-vinylimidazole or methacrylic acid and N-(tert-butyl)aminoethyl (meth)acrylate and from 0 to 35% by weight of vinylpyrrolidone, incorporated in the form of polymerized units.

16. A polyelectrolyte complex comprising at least one ampholytic copolymer, as defined in claim 1, and at least one polyelectrolyte PE) differing therefrom.

17. A cosmetic or pharmaceutical composition comprising
A) at least one ampholytic copolymer, as defined in claim 1, or a polyelectrolyte complex, comprising at least one ampholytic copolymer as defined in claim 1 and at least one polyelectrolyte PE) differing therefrom, and
B) at least one cosmetically or pharmaceutically acceptable carrier.

18. The composition according to claim 17, wherein component B) is selected from the group consisting of
i) water,
ii) water-miscible organic solvents
iii) oils, fats, waxes,
iv) esters of $C_6$-$C_{30}$-monocarboxylic acids with monohydric, dihydric or trihydric alcohols, which esters differ from iii),
v) saturated acyclic and cyclic hydrocarbons,
vi) fatty acids,
vii) fatty alcohols,
viii) propellants
and mixtures thereof.

19. The composition according to claim 17, comprising at least one additive which differs from the components A) and B) and is selected from the group consisting of cosmetically active substances, emulsifiers, surfactants, preservatives, perfume oils, thickeners, hair polymers, hair and skin conditioners, graft polymers, water-soluble or dispersible silicone-containing polymers, light stabilizers, bleaches, gel formers, care compositions, colorants, tinting compositions, tanning compositions, dyes, pigments, consistency agents, moisturizers, refatting agents, collagen, protein hydrolysis products, lipids, antioxidants, antifoams, antistatic agents, emollients and plasticizers.

20. The composition according to claim 17 in the form of a gel, of a foam, of a spray or of a mousse, ointment, cream, emulsion, suspension, lotion, milk or paste.

21. The cosmetic or pharmaceutical composition according to claim 17, wherein the composition is a skin cleansing composition, a composition for the care and for the protection of the skin, a nail care composition, a formulation for decorative cosmetics or a hair treatment composition.

22. The cosmetic or pharmaceutical composition according to claim 17, wherein the composition is a hair setting composition and/or a hair conditioner.

23. The composition according to claim 22, wherein the composition is in the form of a hair gel, shampoo, foam setting composition, hair lotion, hairspray or hair foam.

24. A coating material for a solid dosage form comprising the cosmetic or pharmaceutical composition according to claim 17.

25. A rheological modifier comprising the ampholytic copolymer as claimed in claim 1.

26. An adhesive comprising the ampholytic copolymer as claimed in claim 1.

27. A coating comprising the ampholytic copolymer as claimed in claim 1.

28. An article coated with the ampholytic copolymer as claimed in claim 1.

29. The coated article as claimed in claim 28, wherein the article is textile, paper, print or leather.

30. An ampholytic copolymer comprising a molar excess of anionogenic and/or anionic groups, obtained by free radical polymerization of
a) at least one branched $C_3$-$C_5$-alkyl acrylate,
b) acrylic acid and/or methacrylic acid,
c) a monomer composition comprising
c1) at least one compound having an $\alpha,\beta$-ethylenically unsaturated double bond capable of free radical polymerization and at least one anionogenic and/or anionic group per molecule,
c2) at least one compound having an $\alpha,\beta$-ethylenically unsaturated double bond capable of free radical polymerization and at least one cationogenic and/or cationic group per molecule, and
d) at least one N-vinyllactam incorporated in the form of polymerized units, the molar ratio of anionogenic and anionic groups of component c1) to cationogenic and cationic groups of component c2) being about 1:1.

31. The copolymer according to claim 30, further comprising incorporating in the form of polymerized units, at least one additional monomer e) which is selected from esters, differing from component a), of $\alpha,\beta$-ethylenically unsaturated mono- and dicarboxylic acids with $C_1$-$C_{30}$-alkanols and $C_1$-$C_{30}$-alkanediols, amides of $\alpha,\beta$-ethylenically unsaturated mono- and dicarboxylic acids with $C_2$-$C_{30}$-amino alcohols which have a primary or secondary amino group, N-vinylamides of saturated monocarboxylic acids, primary amides of $\alpha,\beta$-ethylenically unsaturated monocarboxylic acids and the N-alkyl and N,N-dialkyl derivatives thereof, esters of vinyl alcohol and allyl alcohol with $C_1$-$C_{30}$-monocarboxylic acids, vinyl ethers, vinylaromatics, vinyl halides, vinylidene halides, $C_1$-$C_8$-monoolefins, nonaromatic hydrocarbons having at least two conjugated double bonds and mixtures thereof.

32. The copolymer according to claim 31, wherein component e) is selected from the group consisting of $C_1$-$C_3$-alkyl methacrylates, hydroxy-$C_1$-$C_3$-alkyl methacrylates and mixtures thereof.

33. The copolymer according to claim 32, wherein component e) comprises or consists of ethyl methacrylate.

34. The copolymer according to claim 31, comprising:
from 20 to 90% by weight of at least one compound a),
from 5 to 40% by weight of acrylic acid and/or methacrylic acid b),
from 0.5 to 25% by weight of a monomer composition c),
from 1 to 60% by weight of at least one compound d),
from 0 to 25% by weight of at least one compound e),
from 0 to 5% by weight of at least one crosslinking agent f),
incorporated in the form of polymerized units.

35. The copolymer according to claim 30, the component a) comprising tert-butyl acrylate.

36. The copolymer according to claim 30, wherein component c1) is selected from the group consisting of α,β-ethylenically unsaturated mono- and dicarboxylic acids, sulfonic acids, phosphonic acids and mixtures thereof.

37. The copolymer according to claim 30, wherein component c1) is selected from the group consisting of acrylic acid, methacrylic acid, itaconic acid and mixtures thereof.

38. The copolymer according to claim 30, wherein component c2) is selected from the group consisting of esters of α,β-ethylenically unsaturated mono- and dicarboxylic acids with amino alcohols which may be mono- or dialkylated at the amine nitrogen, amides of α,β-ethylenically unsaturated mono- and dicarboxylic acids with diamines which have at least one primary and secondary amino group, N,N-diallylamine, N,N-diallyl-N-alkylamines and the derivatives thereof, vinyl- and allyl-substituted nitrogen heterocycles, vinyl- and allyl-substituted heteroaromatic compounds and mixtures thereof.

39. The copolymer according to claim 30, wherein component c2) is selected from the group consisting of N-vinylimidazole, N-(tert-butylamino)ethyl (meth)acrylate, N,N-dimethylaminoethyl (meth)acrylate, N-[3-(dimethylamino)propyl](meth)acrylamide and mixtures thereof.

40. A polyelectrolyte complex comprising at least one ampholytic copolymer, as defined in claim 30, and at least one polyelectrolyte PE) differing therefrom.

41. A cosmetic or pharmaceutical composition comprising
A) at least one ampholytic copolymer, as defined in claim 30, or a polyelectrolyte complex, comprising at least one ampholytic copolymer as defined in claim 30 and at least one polyelectrolyte PE) differing therefrom, and
B) at least one cosmetically or pharmaceutically acceptable carrier.

42. The composition according to claim 41, wherein component B) is selected from the group consisting of
i) water,
ii) water-miscible organic solvents,
iii) oils, fats, waxes,
iv) esters of $C_6$-$C_{30}$-monocarboxylic acids with monohydric, dihydric or trihydric alcohols, which esters differ from iii),
v) saturated acyclic and cyclic hydrocarbons,
vi) fatty acids,
vii) fatty alcohols,
viii) propellants,
and mixtures thereof.

43. The composition according to claim 41, comprising at least one additive which differs from the components A) and B) and is selected from the group consisting of cosmetically active substances, emulsifiers, surfactants, preservatives, perfume oils, thickeners, hair polymers, hair and skin conditioners, graft polymers, water-soluble or dispersible silicone-containing polymers, light stabilizers, bleaches, gel formers, care compositions, colorants, tinting compositions, tanning compositions, dyes, pigments, consistency agents, moisturizers, refatting agents, collagen, protein hydrolysis products, lipids, antioxidants, antifoams, antistatic agents, emollients and plasticizers.

44. The composition according to claim 41 in the form of a gel, of a foam, of a spray or of a mousse, ointment, cream, emulsion, suspension, lotion, milk or paste.

45. The cosmetic or pharmaceutical composition according to claim 41, wherein the composition is a skin cleansing composition, a composition for the care and for the protection of the skin, a nail care composition, a formulation for decorative cosmetics or a hair treatment composition.

46. The cosmetic or pharmaceutical composition according to claim 41, wherein the composition is a hair setting composition and/or a hair conditioner.

47. The composition according to claim 46, wherein the composition is in the form of a hair gel, shampoo, foam setting composition, hair lotion, hairspray or hair foam.

48. A coating material for a solid dosage form comprising the cosmetic or pharmaceutical composition according to claim 41.

49. A rheological modifier comprising the ampholytic copolymer as claimed in claim 30.

50. An adhesive comprising the ampholytic copolymer as claimed in claim 30.

51. A coating comprising the ampholytic copolymer as claimed in claim 30.

52. An article coated with the ampholytic copolymer as claimed in claim 30.

53. The coated article as claimed in claim 52, wherein the article is textile, paper, print or leather.

\* \* \* \* \*